US006475780B1

(12) United States Patent
Parrington et al.

(10) Patent No.: US 6,475,780 B1
(45) Date of Patent: Nov. 5, 2002

(54) ALPHAVIRUS VECTORS FOR PARAMYXOVIRUS VACCINES

(75) Inventors: Mark Parrington, Bradford; Xiaomao Li; Michel H. Klein, both of Toronto, all of (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 09/554,337

(22) PCT Filed: Nov. 13, 1998

(86) PCT No.: PCT/CA98/01064

§ 371 (c)(1), (2), (4) Date: Oct. 26, 2000

(87) PCT Pub. No.: WO99/25858

PCT Pub. Date: May 27, 2000

Related U.S. Application Data

(60) Provisional application No. 60/065,791, filed on Nov. 14, 1997.

(51) Int. Cl.[7] .......................... C12N 15/63; C12N 15/00

(52) U.S. Cl. ................. 435/320.1; 435/69.1; 435/91.41

(58) Field of Search ......................... 514/44; 435/320.1, 435/69.1, 91.41

(56) References Cited

U.S. PATENT DOCUMENTS

| | | | |
|---|---|---|---|
| 5,284,764 A | 2/1994 | Wathen | |
| 5,814,482 A * | 9/1998 | Dubensky, Jr. et al. | 435/69.3 |
| 5,843,723 A | 12/1998 | Dubensky, Jr. et al. | |
| 5,843,913 A | 12/1998 | Li et al. | |
| 6,060,308 A * | 5/2000 | Parrington | 435/320.1 |
| 6,606,308 | 5/2000 | Parrington | |

FOREIGN PATENT DOCUMENTS

| | | |
|---|---|---|
| WO | WO 92 10578 | 6/1992 |
| WO | WO95/27044 * | 3/1995 |
| WO | WO 95 27044 A | 10/1995 |
| WO | WO 95 27069 | 10/1995 |
| WO | WO 96 17072 A | 6/1996 |
| WO | WO 96 40945 A | 12/1996 |
| WO | WO 99 11808 A | 3/1999 |
| WO | WO 99/25858 | 5/1999 |

OTHER PUBLICATIONS

McIntosh K. and Chanock R.M. in Fields B.N. and Knipe D.M. (eds). Virology. Raven Press, New York, 1990, pp. 1045–1072.

Murphy B.R., Hall S.L., Kulkarni A.B., Crowe J.E., Collins P.L., Connors M., Karron R.A. and Chanock R.M., Virus Res 32, 13–36, 1994.

(List continued on next page.)

*Primary Examiner*—James Ketter
*Assistant Examiner*—Qian J Li
(74) *Attorney, Agent, or Firm*—Sim & McBurney

(57) ABSTRACT

A DNA vector comprises a first DNA sequence which is complementary to at least part of an alphavirus RNA genome and having the complement of complete alphavirus DNA genome replication regions, and a second DNA sequence encoding a paramyxovirus protein, particularly a respiratory syncytial virus fusion (RSV F) protein or a RSV F protein fragment that generates antibodies that specifically react with RSV F protein, the first and second DNA sequences being under the transcriptional control of a promoter, preferably a cytomegalovirus promoter, which may include Intron A. Such vectors also contain a further nucleotide sequence located between the promoter sequence and the alphavirus sequence to enhance the immunoprotective ability of the RSV F protein when expressed in vivo. Such DNA vectors may be used to immunize a host against disease caused by infection with RSV or other paramyxovirus, including a human host, by administration thereto, and may be formulated as immunogenic compositions with pharmaceutically-acceptable carriers for such purposes. Such vectors also may be used to produce antibodies for detection of RSV or other paramyxovirus infection in a sample.

17 Claims, 22 Drawing Sheets

Construction of pMP41 pCMV
VR1012
4912 bp
Intron A
Pst I
Restrict with Pst I
Ligate rabbit β-globin intron II pCMV
pIIE
5580 bp
Intron A
Rabbit β-globin intron II
Sal I 2543
Eco RV 2580
Bam HI 2590
Restrict with Sal I/EcoRV
+Sal I/EcoRV PCR fragment from pSFV1
Ligate Kan
pCMV
pMP38
5843 bp
Intron A
Rabbit β-globin intron II
SFV 5' end
Sal I
Eco RV
Bam HI

OTHER PUBLICATIONS

Osterweil D. and Norman D., Am Geriat Soc 36, 659–662, 1990.
Agius G., Dindinand G., Biggar R.J., Peyre R., Vaillant V., Ranger S., Poupet J.Y., Cisse M.F. and Casters M., J Med Virol 30, 117–127, 1990.
Katz S.L. in New vaccine development establishing priorities vol. 1. National Academic Press, Washington, 1985, pp. 397–4 09.
Wertz G.W. and Sullender W.M., Biotechnology 20, 151–176, 1992.
Fulginiti V.A., Eller J.J., Sieber O.F., Joyner J.W., Minamitani M. and Meiklejohn G., Am J. Epidemiol 89, 49–463, 1969.
Chin J., Magoffin R.L., Shearer I.A., Schieble J.H. and Lennette E.H., Am J Epidemiol 89, 449–463 1969.
Belshe R.B., Van Voris L.P. and Mufson M.A., J Infect Dis 145, 311–319, 1982.
Kim R.M., Arrobio J.O., Pyles G., Brandt C.D., Camargo E., Chanock R.M. and Parrott R.H., Pediatrics 48, 745–755, 1971.
Gruber C. and Levine S., J Gen Virol 64, 825–832, 1983.
Olmstead R.A., Elango N. and Prince G.A., Proc Natl Acad Sci USA 83, 7462–7466, 1991.
Parrington M., Cockle S., Wyde P., Du R.–P., Snell E., Yan W.–Y., Wang Q., Gisonni L., Sanhueza S., Ewasyshyn M. and Klein M., Virus Genes 14, 65–74, 1997.
Fulginiti, V.A., Eller, J.J., Sieber, O.F., Joyner, J.W., Minamitani, M. and Meiklejohn, G. (1969) Am. J. Epidemiol. 89(4), 435–448.
Chin, J., Magoffin, R.L., Shearer, L.A., Schieble, J.H. and Lennette, E.H. (1969) Am. J. Epidemiol. 89(4), 449–463.
Jensen, K.E., Peeler, B.E. and Dulworth, W.G. (1962) J. Immunol. 89, 216–226.
Murphy, B.R., Prince, G.A., Collins, P.L., Van Wyke –Coelingh, K., Olmsted, R.A., Spriggs, M.K, Parrott, R.H., Kim, H.–Y., Brandt, C.D. and Chanock, R.M. (1988) Vir. Res. 11, 1–15.
Hall, S.L., Sarris, C.M., Tierney, E.L., London, W.T., and Murphy, B.R. (1993) J. Infect. Dis. 167, 958–962.
Belshe, R.B., Karron, R.A., Newman, F.K., Anderson, E.L., Nugent, S.L., Steinhoff, M., Clements, M.L., Wilson, M.H., Hall, S.L., Tierney, E.L. and Murphy, B.R. (1992) J. Clin. Microbiol. 30(8), 2064–2070.
Hall, S.L., Stokes, A., Tierney, E.L., London, W.T., Belshe, R.B., Newman, F.C. and Murphy, B.R. (1992) Vir. Res. 22, 173–184.
Van Wyke Coelingh, K.L., Winter, C.C., Tierney, E.L., London, W.T. and Murphy, B.R. (1988) J. Infect. Dis. 157 (4), 655–662.
Ray, R., Novak, M., Duncan, J.D., Matsuoka, Y. and Compans, R.W. (1993) J. Infect. Dis. 167, 752–755.
Ray, R., Brown, V.E. and Compans, R.W. (1985) J. Infect. Dis. 152 (6), 1219–1230.
Ray, R. and Compans, R.W. (1987) J. Gen. Virol. 68, 409–418.
Ray, R., Glaze, B.J., Moldoveanu, Z. and Compans, R.W. (1988) J. Infect. Dis. 157 (4), 648–654.
Ray, R., Matsuoka, Y., Burnett, T.L., Glaze, B.J. and Compans, R.W. (1990) J. Infect. Dis. 162, 746–749.
Ray, R., Glaze, B.J. and Compans, R.W. (1988) J. Virol. 62 (3), 783–787.
Ewasyshyn, M., Caplan, B., Bonneau A.–M., Scollard, N., Graham, S., Usman, S. and Klein, M. (1992) Vaccine 10 (6), 412–420.
Ambrose, M.W., Wyoe, P.R., Ewasyshyn, M., Bonneau, A.–M., Caplan, B., Meyer, H.L. and Klein, M. (1991) Vaccine 9, 505–511.
Kasel, J.A., Frank, A.L., Keitel, W.H., Taber, L.H., Glezen W.P. J. Virol. 1984; 52:828–32.
Lehman, D.J., Roof, L.L., Brideau, R.J., Aeed, P.A., Thomsen, D.R., Elhammer, A.P., Wathen, M.W. and Homa, F.L. (1993) J. Gen. Virol. 74, 459–469.
Brideau, R.J., Oien, N.L., Lehman, D.J., Homa, F.L. and Wathen, M.W. (1993) J. Gen. Virol. 74, 471–477.
Ebata, S.N., Prevec, L., Graham, F.L. and Dimock, K. (1992) Vir. Res. 24, 21–33.
Hall, S.L., Murphy, B.R. and Van Wyke Coelingh, K.L. (1991) Vaccine 9, 659–667.
Strauss E.G. and Strauss J.H., in Schlesinger S.S. and Schlesinger M. (eds). The Togaviridae and Flaviviridae. Plenum Press, New York, 1986, pp. 35–90.
Chapman, B.S.; Thayer, R.M.; Vincent, K.A. and Haigwood, N.L., Nucl. Acids. Res. 1991, 19:3979–3986.
Breathnach, R. and Harris, B.A., Nucl. Acids Res. 1983, 11:7119–7136.
Nabel, G.J. 1993, Proc. Natl. Acad. Sci. USA 90:11307–11311.
Tang et al., Nature 1992, 356:152–154.
Furth et al. Analytical Biochemistry, 1992, 205:365–368.
Prince, G.A. et al, Am. J. Pathol. 93, 771 to 790, 1978.
Zhou, X. et al Vaccine, vol. 12, No. 16, 1994, pp. 1510–1514.
Liljestroem, P. et al Biotechnology, vol. 9, Dec. 1991, pp. 1356–1361.
Bousse Tatiana, Takimoto T., Gopal Murti K., Portner A. Virology 232, 44–52 (1997).
Dalemans W. et al Protection against Homologous Influenza. pp. 255–256.
Ray R., Meyer K., Newman K.F., Belshe B.R., Journal of Virology, Mar., (1995), p. 1959–1963.
Huang Zhi–Ming, Benedict Yen. Molecular and Cellular Biology, Jul. 1995, p3864–3869.
SFV Gene Expression System p. 18–31.

* cited by examiner

FIG.3A

Nucleotide sequence of plasmid pMP44

```
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcatataatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga ctttccattg acgtcaatgg gtggagtatt tacggtaaac 540
tgcccacttg gcagtacatc aagtgtatca tatgccaagt acgcccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctccg cggccgggaa cggtgcattg gaacgcggat 1020
tccccgtgcc aagagtgacg taagtaccgc ctatagactc tataggcaca cccctttggc 1080
tcttatgcat gctatactgt ttttggcttg gggcctatac acccccgctt ccttatgcta 1140
taggtgatgg tatagcttag cctataggtg tgggttattg accattattg accactcccc 1200
tattggtgac gatactttcc attactaatc cataacatgg ctctttgcca caactatctc 1260
tattggctat atgccaatac tctgtccttc agagactgac acggactctg tatttttaca 1320
ggatggggtc ccatttatta tttacaaatt cacatataca acaacgccgt cccccgtgcc 1380
cgcagttttt attaaacata gcgtgggatc tccacgcgaa tctcgggtac gtgttccgga 1440
catgggctct tctccggtag cggcggagct tccacatccg agccctggtc ccatgcctcc 1500
```

FIG.3B

```
agcggctcat ggtcgctcgg cagctccttg ctcctaacag tggaggccag acttaggcac 1560
agcacaatgc ccaccaccac cagtgtgccg cacaaggccg tggcggtagg gtatgtgtct 1620
gaaaatgagc gtggagattg ggctcgcacg gctgacgcag atggaagact taaggcagcg 1680
gcagaagaag atgcaggcag ctgagttgtt gtattctgat aagagtcaga ggtaactccc 1740
gttgcggtgc tgttaacggt ggagggcagt gtagtctgag cagtactcgt tgctgccgcg 1800
cgcgccacca gacataatag ctgacagact aacagactgt tcctttccat gggtcttttc 1860
cgatcctgag aacttcaggg tgagtttggg gacccttgat tgttctttct ttttcgctat 1920
tgtaaaattc atgttatatg gagggggcaa agttttcagg gtgttgttta gaatgggaag 1980
atgtcccttg tatcaccatg gaccctcatg ataattttgt ttctttcact ttctactctg 2040
ttgacaacca ttgtctcctc ttattttctt ttcattttct gtaacttttt cgttaaactt 2100
tagcttgcat ttgtaacgaa tttttaaatt cacttttgtt tatttgtcag attgtaagta 2160
ctttctctaa tcactttttt ttcaaggcaa tcagggtata ttatattgta cttcagcaca 2220
gttttagaga acaattgtta taattaaatg ataaggtaga atatttctgc atataaattc 2280
tggctggcgt ggaaatattc ttattggtag aaacaactac atcctggtca tcatcctgcc 2340
tttctcttta tggttacaat gatatacact gtttgagatg aggataaaat actctgagtc 2400
caaaccgggc ccctctgcta accatgttca tgccttcttc tttttcctac agctcctggg 2460
caacgtgctg gttattgtgc tgtctcatca ttttggcaaa gaattgtaat acgactcact 2520
atagggcgaa ttgtcaccgt cgtcgacatg gcggatgtgt gacatacacg acgccaaaag 2580
attttgttcc agctcctgcc acctccgcta cgcgagagat taaccaccca cgatggccgc 2640
caaagtgcat gttgatattg aggctgacag cccattcatc aagtctttgc agaaggcatt 2700
tccgtcgttc gaggtggagt cattgcaggt cacaccaaat gaccatgcaa atgccagagc 2760
attttcgcac ctggctacca aattgatcga gcaggagact gacaaagaca cactcatctt 2820
ggatatcggc agtgcgcctt ccaggagaat gatgtctacg cacaaatacc actgcgtatg 2880
ccctatgcgc agcgcagaag accccgaaag gctcgatagc tacgcaaaga aactggcagc 2940
ggcctccggg aaggtgctgg atagagagat cgcaggaaaa atcaccgacc tgcagaccgt 3000
catggctacg ccagacgctg aatctcctac cttttgcctg catacagacg tcacgtgtcg 3060
tacggcagcc gaagtggccg tataccagga cgtgtatgct gtacatgcac caacatcgct 3120
```

FIG.3C

```
gtaccatcag gcgatgaaag gtgtcagaac ggcgtattgg attgggtttg acaccacccc 3180
gtttatgttt gacgcgctag caggcgcgta tccaacctac gccacaaact gggccgacga 3240
gcaggtgtta caggccagga acataggact gtgtgcagca tccttgactg agggaagact 3300
cggcaaactg tccattctcc gcaagaagca attgaaacct tgcgacacag tcatgttctc 3360
ggtaggatct acattgtaca ctgagagcag aaagctactg aggagctggc acttaccctc 3420
cgtattccac ctgaaaggta aacaatcctt tacctgtagg tgcgatacca tcgtatcatg 3480
tgaagggtac gtagttaaga aaatcactat gtgccccggc ctgtacggta aaacggtagg 3540
gtacgccgtg acgtatcacg cggagggatt cctagtgtgc aagaccacag acactgtcaa 3600
aggagaaaga gtctcattcc ctgtatgcac ctacgtcccc tcaaccatct gtgatcaaat 3660
gactggcata ctagcgaccg acgtcacacc ggaggacgca cagaagttgt tagtgggatt 3720
gaatcagagg atagttgtga acggaagaac acagcgaaac actaacacga tgaagaacta 3780
tctgcttccg attgtggccg tcgcatttag caagtgggcg agggaataca aggcagacct 3840
tgatgatgaa aaacctctgg gtgtccgaga gaggtcactt acttgctgct gcttgtgggc 3900
atttaaaacg aggaagatgc acaccatgta caagaaacca gacacccaga caatagtgaa 3960
ggtgccttca gagtttaact cgttcgtcat cccgagccta tggtctacag gcctcgcaat 4020
cccagtcaga tcacgcatta agatgctttt ggccaagaag accaagcgag agttaatacc 4080
tgttctcgac gcgtcgtcag ccagggatgc tgaacaagag gagaaggaga ggttggaggc 4140
cgagctgact agagaagcct taccacccct cgtccccatc gcgccggcgg agacgggagt 4200
cgtcgacgtc gacgttgaag aactagagta tcacgcaggt gcaggggtcg tggaaacacc 4260
tcgcagcgcg ttgaaagtca ccgcacagcc gaacgacgta ctactaggaa attacgtagt 4320
tctgtccccg cagaccgtgc tcaagagctc caagttggcc cccgtgcacc ctctagcaga 4380
gcaggtgaaa ataataacac ataacgggag ggccggcggt taccaggtcg acggatatga 4440
cggcagggtc ctactaccat gtggatcggc cattccggtc cctgagtttc aagctttgag 4500
cgagagcgcc actatggtgt acaacgaaag ggagttcgtc aacaggaaac tataccatat 4560
tgccgttcac ggaccgtcgc tgaacaccga cgaggagaac tacgagaaag tcagagctga 4620
aagaactgac gccgagtacg tgttcgacgt agataaaaaa tgctgcgtca agagagagga 4680
agcgtcgggt ttggtgttgg tgggagagct aaccaacccc ccgttccatg aattcgccta 4740
```

FIG.3D

```
cgaagggctg aagatcaggc cgtcggcacc atataagact acagtagtag gagtctttgg 4800
ggttccggga tcaggcaagt ctgctattat taagagcctc gtgaccaaac acgatctggt 4860
caccagcggc aagaaggaga actgccagga aatagttaac gacgtgaaga agcaccgcgg 4920
gaaggggaca agtagggaaa acagtgactc catcctgcta aacgggtgtc gtcgtgccgt 4980
ggacatccta tatgtggacg aggctttcgc ttgccattcc ggtactctgc tggccctaat 5040
tgctcttgtt aaacctcgga gcaaagtggt gttatgcgga gaccccaagc aatgcggatt 5100
cttcaatatg atgcagctta aggtgaactt caaccacaac atctgcactg aagtatgtca 5160
taaaagtata tccagacgtt gcacgcgtcc agtcacggcc atcgtgtcta cgttgcacta 5220
cggaggcaag atgcgcacga ccaacccgtg caacaaaccc ataatcatag acaccacagg 5280
acagaccaag cccaagccag gagacatcgt gttaacatgc ttccgaggct gggcaaagca 5340
gctgcagttg gactaccgtg gacacgaagt catgacagca gcagcatctc agggcctcac 5400
ccgcaaaggg gtatacgccg taaggcagaa ggtgaatgaa aatcccttgt atgcccctgc 5460
gtcggagcac gtgaatgtac tgctgacgcg cactgaggat aggctggtgt ggaaaacgct 5520
ggccggcgat ccctggatta aggtcctatc aaacattcca cagggtaact ttacggccac 5580
attggaagaa tggcaagaag aacacgacaa aataatgaag gtgattgaag gaccggctgc 5640
gcctgtggac gcgttccaga acaaagcgaa cgtgtgttgg gcgaaaagcc tggtgcctgt 5700
cctggacact gccggaatca gattgacagc agaggagtgg agcaccataa ttacagcatt 5760
taaggaggac agagcttact ctccagtggt ggccttgaat gaaatttgca ccaagtacta 5820
tggagttgac ctggacagtg gcctgttttc tgccccgaag gtgtccctgt attacgagaa 5880
caaccactgg gataacagac ctggtggaag gatgtatgga ttcaatgccg caacagctgc 5940
caggctggaa gctagacata ccttcctgaa ggggcagtgg catacgggca agcaggcagt 6000
tatcgcagaa agaaaaatcc aaccgctttc tgtgctggac aatgtaattc ctatcaaccg 6060
caggctgccg cacgccctgg tggctgagta caagacggtt aaaggcagta gggttgagtg 6120
gctggtcaat aaagtaagag ggtaccacgt cctgctggtg agtgagtaca acctggcttt 6180
gcctcgacgc agggtcactt ggttgtcacc gctgaatgtc acaggcgccg ataggtgcta 6240
cgacctaagt ttaggactgc cggctgacgc cggcaggttc gacttggtct ttgtgaacat 6300
tcacacggaa ttcagaatcc accactacca gcagtgtgtc gaccacgcca tgaagctgca 6360
```

FIG.3E

```
gatgcttggg ggagatgcgc tacgactgct aaaacccggc ggcatcttga tgagagctta 6420
cggatacgcc gataaaatca gcgaagccgt tgtttcctcc ttaagcagaa agttctcgtc 6480
tgcaagagtg ttgcgcccgg attgtgtcac cagcaataca gaagtgttct tgctgttctc 6540
caactttgac aacggaaaga gaccctctac gctacaccag atgaatacca agctgagtgc 6600
cgtgtatgcc ggagaagcca tgcacacggc cgggtgtgca ccatcctaca gagttaagag 6660
agcagacata gccacgtgca cagaagcggc tgtggttaac gcagctaacg cccgtggaac 6720
tgtaggggat ggcgtatgca gggccgtggc gaagaaatgg ccgtcagcct ttaagggagc 6780
agcaacacca gtgggcacaa ttaaaacagt catgtgcggc tcgtaccccg tcatccacgc 6840
tgtagcgcct aatttctctg ccacgactga agcggaaggg gaccgcgaat tggccgctgt 6900
ctaccgggca gtggccgccg aagtaaacag actgtcactg agcagcgtag ccatcccgct 6960
gctgtccaca ggagtgttca gcggcggaag agataggctg cagcaatccc tcaaccatct 7020
attcacagca atggacgcca cggacgctga cgtgaccatc tactgcagag acaaaagttg 7080
ggagaagaaa atccaggaag ccattgacat gaggacggct gtggagttgc tcaatgatga 7140
cgtggagctg accacagact tggtgagagt gcacccggac agcagcctgg tgggtcgtaa 7200
gggctacagt accactgacg ggtcgctgta ctcgtacttt gaaggtacga aattcaacca 7260
ggctgctatt gatatggcag agatactgac gttgtggccc agactgcaag aggcaaacga 7320
acagatatgc ctatacgcgc tgggcgaaac aatggacaac atcagatcca aatgtccggt 7380
gaacgattcc gattcatcaa cacctcccag gacagtgccc tgcctgtgcc gctacgcaat 7440
gacagcagaa cggatcgccc gccttaggtc acaccaagtt aaaagcatgg tggtttgctc 7500
atcttttccc ctcccgaaat accatgtaga tggggtgcag aaggtaaagt gcgagaaggt 7560
tctcctgttc gacccgacgg taccttcagt ggttagtccg cggaagtatg ccgcatctac 7620
gacggaccac tcagatcggt cgttacgagg gtttgacttg gactggacca ccgactcgtc 7680
ttccactgcc agcgatacca tgtcgctacc cagtttgcag tcgtgtgaca tcgactcgat 7740
ctacgagcca atggctccca tagtagtgac ggctgacgta caccctgaac ccgcaggcat 7800
cgcggacctg gcggcagatg tgcaccctga acccgcagac catgtggacc tcgagaaccc 7860
gattcctcca ccgcgcccga agagagctgc ataccttgcc tcccgcgcgg cggagcgacc 7920
ggtgccggcg ccgagaaagc cgacgcctgc cccaaggact gcgtttagga acaagctgcc 7980
```

FIG.3F

```
tttgacgttc ggcgactttg acgagcacga ggtcgatgcg ttggcctccg ggattacttt 8040
cggagacttc gacgacgtcc tgcgactagg ccgcgcgggt gcatatattt tctcctcgga 8100
cactggcagc ggacatttac aacaaaaatc cgttaggcag cacaatctcc agtgcgcaca 8160
actggatgcg gtccaggagg agaaaatgta cccgccaaaa ttggatactg agagggagaa 8220
gctgttgctg ctgaaaatgc agatgcaccc atcggaggct aataagagtc gataccagtc 8280
tcgcaaagtg gagaacatga aagccacggt ggtggacagg ctcacatcgg gggccagatt 8340
gtacacggga gcggacgtag gccgcatacc aacatacgcg gttcggtacc cccgccccgt 8400
gtactcccct accgtgatcg aaagattctc aagccccgat gtagcaatcg cagcgtgcaa 8460
cgaataccta tccagaaatt acccaacagt ggcgtcgtac cagataacag atgaatacga 8520
cgcatacttg gacatggttg acgggtcgga tagttgcttg gacagagcga cattctgccc 8580
ggcgaagctc cggtgctacc cgaaacatca tgcgtaccac cagccgactg tacgcagtgc 8640
cgtcccgtca ccctttcaga acacactaca gaacgtgcta gcggccgcca ccaagagaaa 8700
ctgcaacgtc acgcaaatgc gagaactacc caccatggac tcggcagtgt tcaacgtgga 8760
gtgcttcaag cgctatgcct gctccggaga atattgggaa gaatatgcta aacaacctat 8820
ccggataacc actgagaaca tcactaccta tgtgaccaaa ttgaaaggcc cgaaagctgc 8880
tgccttgttc gctaagaccc acaacttggt tccgctgcag gaggttccca tggacagatt 8940
cacggtcgac atgaaacgag atgtcaaagt cactccaggg acgaaacaca cagaggaaag 9000
acccaaagtc caggtaattc aagcagcgga gccattggcg accgcttacc tgtgcggcat 9060
ccacagggaa ttagtaagga gactaaatgc tgtgttacgc cctaacgtgc acacattgtt 9120
tgatatgtcg gccgaagact ttgacgcgat catcgcctct cacttccacc caggagaccc 9180
ggttctagag acggacattg catcattcga caaaagccag gacgactcct tggctcttac 9240
aggtttaatg atcctcgaag atctaggggt ggatcagtac ctgctggact tgatcgaggc 9300
agcctttggg gaaatatcca gctgtcacct accaactggc acgcgcttca agttcggagc 9360
tatgatgaaa tcgggcatgt ttctgacttt gtttattaac actgttttga acatcaccat 9420
agcaagcagg gtactggagc agagactcac tgactccgcc tgtgcggcct tcatcggcga 9480
cgacaacatc gttcacggag tgatctccga caagctgatg gcggagaggt gcgcgtcgtg 9540
ggtcaacatg gaggtgaaga tcattgacgc tgtcatgggc gaaaaacccc catatttttg 9600
```

FIG.3G

```
tgggggattc atagtttttg acagcgtcac acagaccgcc tgccgtgttt cagacccact 9660
taagcgcctg ttcaagttgg gtaagccgct aacagctgaa gacaagcagg acgaagacag 9720
gcgacgagca ctgagtgacg aggttagcaa gtggttccgg acaggcttgg gggccgaact 9780
ggaggtggca ctaacatcta ggtatgaggt agagggctgc aaaagtatcc tcatagccat 9840
ggccaccttg gcgagggaca ttaaggcgtt taagaaattg agaggacctg ttatacacct 9900
ctacggcggt cctagattgg tgcgttaata cacagaattc tgattggatc atagcgcact 9960
attataggat ccgcgcgcgc gaattcggca cgagtaacaa tggagttgct aatcctcaaa 10020
gcaaatgcaa ttaccacaat cctcactgca gtcacatttt gttttgcttc tggtcaaaac 10080
atcactgaag aattttatca atcaacatgc agtgcagtta gcaaaggcta tcttagtgct 10140
ctgagaactg gttggtatac cagtgttata actatagaat taagtaatat caaggaaaat 10200
aagtgtaatg gaacagatgc taaggtaaaa ttgataaaac aagaattaga taaatataaa 10260
aatgctgtaa cagaattgca gttgctcatg caaagcacac cagcagcaaa caatcgagcc 10320
agaagagaac taccaaggtt tatgaattat acactcaaca atgccaaaaa aaccaatgta 10380
acattaagca agaaaaggaa aagaagattt cttggttttt tgttaggtgt tggatctgca 10440
atcgccagtg gcgttgctgt atctaaggtc ctgcacctag aaggggaagt gaacaagatc 10500
aaaagtgctc tactatccac aaacaaggct gtagtcagct tatcaaatgg agttagtgtc 10560
ttaaccagca aagtgttaga cctcaaaaac tatatagata aacaattgtt acctattgtg 10620
aacaagcaaa gctgcagcat atcaaatata gaaactgtga tagagttcca acaaaagaac 10680
aacagactac tagagattac cagggaattt agtgttaatg caggtgtaac tacacctgta 10740
agcacttaca tgttaactaa tagtgaatta ttgtcattaa tcaatgatat gcctataaca 10800
aatgatcaga aaaagttaat gtccaacaat gttcaaatag ttagacagca aagttactct 10860
atcatgtcca taataaaaga ggaagtctta gcatatgtag tacaattacc actatatggt 10920
gttatagata caccctgttg gaaactacac acatcccctc tatgtacaac caacacaaaa 10980
gaagggtcca acatctgttt aacaagaact gacagaggat ggtactgtga caatgcagga 11040
tcagtatctt tcttcccaca agctgaaaca tgtaaagttc aatcaaatcg agtattttgt 11100
gacacaatga acagtttaac attaccaagt gaaataaatc tctgcaatgt tgacatattc 11160
aaccccaaat atgattgtaa aattatgact tcaaaaacag atgtaagcag ctccgttatc 11220
```

FIG.3H

```
acatctctag gagccattgt gtcatgctat ggcaaaacta aatgtacagc atccaataaa 11280
aatcgtggaa tcataaagac attttctaac gggtgcgatt atgtatcaaa taaagggatg 11340
gacactgtgt ctgtaggtaa cacattatat tatgtaaata agcaagaagg taaaagtctc 11400
tatgtaaaag gtgaaccaat aataaatttc tatgacccat tagtattccc ctctgatgaa 11460
tttgatgcat caatatctca agtcaacgag aagattaacc agagcctagc atttattcgt 11520
aaatccgatg aattattaca taatgtaaat gctggtaaat ccaccacaaa tatcatgact 11580
tgataatgag gatccagatc ccgggtaatt aattgaatta catccctacg caaacgtttt 11640
acggccgccg gtggcgcccg cgcccggcgg cccgtccttg gccgttgcag gccactccgg 11700
tggctcccgt cgtccccgac ttccaggccc agcagatgca gcaactcatc agcgccgtaa 11760
atgcgctgac aatgagacag aacgcaattg ctcctgctag gcctcccaaa ccaaagaaga 11820
agaagacaac caaaccaaag ccgaaaacgc agcccaagaa gatcaacgga aaaacgcagc 11880
agcaaaagaa gaaagacaag caagccgaca agaagaagaa gaaacccgga aaaagagaaa 11940
gaatgtgcat gaagattgaa aatgactgta tcttcgtatg cggctagcca cagtaacgta 12000
gtgtttccag acatgtcggg caccgcacta tcatgggtgc agaaaatctc gggtggtctg 12060
ggggccttcg caatcggcgc tatcctggtg ctggttgtgg tcacttgcat tgggctccgc 12120
agataagtta gggtaggcaa tggcattgat atagcaagaa aattgaaaac agaaaaagtt 12180
agggtaagca atggcatata accataactg tataacttgt aacaaagcgc aacaagacct 12240
gcgcaattgg ccccgtggtc cgcctcacgg aaactcgggg caactcatat tgacacatta 12300
attggcaata attggaagct tacataagct taattcgacg aataattgga tttttatttt 12360
attttgcaat tggtttttaa tatttccaaa aaaaaaaaaa aaaaaaaaaa aaaaaaaaaa 12420
aaaaaaaaaa aaaaaaaaaa aaaaaaaaaa aaaaaaacta gcgggtcggc atggcatctc 12480
cacctcctcg cggtccgacc tgggcatccg aaggaggacg cacgtccact cggatggcta 12540
agggagagat ccagatctgc tgtgccttct agttgccagc catctgttgt ttgcccctcc 12600
cccgtgcctt ccttgaccct ggaaggtgcc actcccactg tcctttccta ataaaatgag 12660
gaaattgcat cgcattgtct gagtaggtgt cattctattc tggggggtgg ggtggggcag 12720
gacagcaagg gggaggattg ggaagacaat agcaggcatg ctggggatgc ggtgggctct 12780
atgggtaccc aggtgctgaa gaattgaccc ggttcctcct gggccagaaa gaagcaggca 12840
```

FIG.3I

```
catccccttc tctgtgacac accctgtcca cgcccctggt tcttagttcc agccccactc 12900
ataggacact catagctcag gagggctccg ccttcaatcc cacccgctaa agtacttgga 12960
gcggtctctc cctccctcat cagcccacca aaccaaacct agcctccaag agtgggaaga 13020
aattaaagca agataggcta ttaagtgcag agggagagaa aatgcctcca acatgtgagg 13080
aagtaatgag agaaatcata gaatttcttc cgcttcctcg ctcactgact cgctgcgctc 13140
ggtcgttcgg ctgcggcgag cggtatcagc tcactcaaag gcggtaatac ggttatccac 13200
agaatcaggg gataacgcag gaaagaacat gtgagcaaaa ggccagcaaa aggccaggaa 13260
ccgtaaaaag gccgcgttgc tggcgttttt ccataggctc cgcccccctg acgagcatca 13320
caaaaatcga cgctcaagtc agaggtggcg aaacccgaca ggactataaa gataccaggc 13380
gtttccccct ggaagctccc tcgtgcgctc tcctgttccg accctgccgc ttaccggata 13440
cctgtccgcc tttctccctt cgggaagcgt ggcgctttct catagctcac gctgtaggta 13500
tctcagttcg gtgtaggtcg ttcgctccaa gctgggctgt gtgcacgaac cccccgttca 13560
gcccgaccgc tgcgccttat ccggtaacta tcgtcttgag tccaacccgg taagacacga 13620
cttatcgcca ctggcagcag ccactggtaa caggattagc agagcgaggt atgtaggcgg 13680
tgctacagag ttcttgaagt ggtggcctaa ctacggctac actagaagaa cagtatttgg 13740
tatctgcgct ctgctgaagc cagttacctt cggaaaaaga gttggtagct cttgatccgg 13800
caaacaaacc accgctggta gcggtggttt ttttgtttgc aagcagcaga ttacgcgcag 13860
aaaaaaagga tctcaagaag atcctttgat cttttctacg gggtctgacg ctcagtggaa 13920
cgaaaactca cgttaaggga ttttggtcat gagattatca aaaaggatct tcacctagat 13980
ccttttaaat taaaaatgaa gttttaaatc aatctaaagt atatatgagt aaacttggtc 14040
tgacagttac caatgcttaa tcagtgaggc acctatctca gcgatctgtc tatttcgttc 14100
atccatagtt gcctgactcg gggggggggg gcgctgaggt ctgcctcgtg aagaaggtgt 14160
tgctgactca taccaggcct gaatcgcccc atcatccagc cagaaagtga gggagccacg 14220
gttgatgaga gctttgttgt aggtggacca gttggtgatt ttgaactttt gctttgccac 14280
ggaacggtct gcgttgtcgg gaagatgcgt gatctgatcc ttcaactcag caaaagttcg 14340
atttattcaa caaagccgcc gtcccgtcaa gtcagcgtaa tgctctgcca gtgttacaac 14400
caattaacca attgtgatta gaaaaactca tcgagcatca aatgaaactg caatttattc 14460
```

FIG.3J

```
atatcaggat tatcaatacc atatttttga aaaagccgtt tctgtaatga aggagaaaac 14520
tcaccgaggc agttccatag gatggcaaga tcctggtatc ggtctgcgat tccgactcgt 14580
ccaacatcaa tacaacctat taatttcccc tcgtcaaaaa taaggttatc aagtgagaaa 14640
tcaccatgag tgacgactga atccggtgag aatggcaaaa gcttatgcat ttctttccag 14700
acttgttcaa caggccagcc attacgctcg tcatcaaaat cactcgcatc aaccaaaccg 14760
ttattcattc gtgattgcgc ctgagcgaga cgaaatacgc gatcgctgtt aaaaggacaa 14820
ttacaaacag gaatcgaatg caaccggcgc aggaacactg ccagcgcatc aacaatattt 14880
tcacctgaat caggatattc ttctaatacc tggaatgctg ttttcccggg gatcgcagtg 14940
gtgagtaacc atgcatcatc aggagtacgg ataaaatgct tgatggtcgg aagaggcata 15000
aattccgtca gccagtttag tctgaccatc tcatctgtaa catcattggc aacgctacct 15060
ttgccatgtt tcagaaacaa ctctggcgca tcgggcttcc catacaatcg atagattgtc 15120
gcacctgatt gcccgacatt atcgcgagcc catttatacc catataaatc agcatccatg 15180
ttggaattta atcgcggcct cgagcaagac gtttcccgtt gaatatggct cataacgttc 15240
cttgtattac tgtttatgta agcagacagt tttattgttc atgatgatat atttttatct 15300
tgtgcaatgt aacatcagag attttgagac acaacgtggc tttccccccc cccccattat 15360
tgaagcattt atcagggtta ttgtctcatg agcggataca tatttgaatg tatttagaaa 15420
aataaacaaa taggggttcc gcgcacattt ccccgaaaag tgccacctga cgtctaagaa 15480
accattatta tcatgacatt aacctataaa aataggcgta tcacgaggcc ctttcgtc   15538
```

Ribozyme linker for pMP42

```
5'                                                                                        3'
CTAGCGGGTCGGCATGGCATCTCCACCTCCTCGCGGTCCGACCTGGGCATCCGAAGGAGGACGCACGTCCACTCGGATGGCTAAGGGAGA
    GCCCAGCCGTACCGTAGAGGTTGAGGAGCGCCAGGCTGGACCCGTAGGCTTCCTCCTGCGTGCAGGTGAGCCTACCGATTCCCTCTCTAG
```

SFV Eco RV-Spe I fragment ligated to ribozyme

```
atcggcagtg cgccttccag gagaatgatg tctacgcaca aataccactg cgtatgccct 60
atgcgcagcg cagaagaccc cgaaaggctc gatagctacg caaagaaact ggcagcggcc 120
tccgggaagg tgctggatag agagatcgca ggaaaaatca ccgacctgca gaccgtcatg 180
gctacgccag acgctgaatc tcctaccttt tgcctgcata cagacgtcac gtgtcgtacg 240
gcagccgaag tggccgtata ccaggacgtg tatgctgtac atgcaccaac atcgctgtac 300
catcaggcga tgaaaggtgt cagaacggcg tattggattg ggtttgacac caccccgttt 360
atgtttgacg cgctagcagg cgcgtatcca acctacgcca caaactgggc cgacgagcag 420
gtgttacagg ccaggaacat aggactgtgt gcagcatcct tgactgaggg aagactcggc 480
aaactgtcca ttctccgcaa gaagcaattg aaaccttgcg acacagtcat gttctcggta 540
ggatctacat tgtacactga gagcagaaag ctactgagga gctggcactt accctccgta 600
ttccacctga aaggtaaaca atcctttacc tgtaggtgcg ataccatcgt atcatgtgaa 660
gggtacgtag ttaagaaaat cactatgtgc cccggcctgt acggtaaaac ggtagggtac 720
gccgtgacgt atcacgcgga gggattccta gtgtgcaaga ccacagacac tgtcaaagga 780
gaaagagtct cattccctgt atgcacctac gtcccctcaa ccatctgtga tcaaatgact 840
ggcatactag cgaccgacgt cacaccggag gacgcacaga agttgttagt gggattgaat 900
cagaggatag ttgtgaacgg aagaacacag cgaaacacta acacgatgaa gaactatctg 960
cttccgattg tggccgtcgc atttagcaag tgggcgaggg aatacaaggc agaccttgat 1020
gatgaaaaac ctctgggtgt ccgagagagg tcacttactt gctgctgctt gtgggcattt 1080
aaaacgagga agatgcacac catgtacaag aaaccagaca cccagacaat agtgaaggtg 1140
ccttcagagt ttaactcgtt cgtcatcccg agcctatggt ctacaggcct cgcaatccca 1200
gtcagatcac gcattaagat gcttttggcc aagaagacca agcgagagtt aatacctgtt 1260
ctcgacgcgt cgtcagccag ggatgctgaa caagaggaga aggagaggtt ggaggccgag 1320
ctgactagag aagccttacc acccctcgtc cccatcgcgc cggcggagac gggagtcgtc 1380
gacgtcgacg ttgaagaact agagtatcac gcaggtgcag gggtcgtgga aacacctcgc 1440
agcgcgttga aagtcaccgc acagccgaac gacgtactac taggaaatta cgtagttctg 1500
```

FIG.6B

```
tccccgcaga ccgtgctcaa gagctccaag ttggcccccg tgcaccctct agcagagcag 1560
gtgaaaataa taacacataa cgggagggcc ggcggttacc aggtcgacgg atatgacggc 1620
agggtcctac taccatgtgg atcggccatt ccggtccctg agtttcaagc tttgagcgag 1680
agcgccacta tggtgtacaa cgaaagggag ttcgtcaaca ggaaactata ccatattgcc 1740
gttcacggac cgtcgctgaa caccgacgag gagaactacg agaaagtcag agctgaaaga 1800
actgacgccg agtacgtgtt cgacgtagat aaaaaatgct gcgtcaagag agaggaagcg 1860
tcgggtttgg tgttggtggg agagctaacc aaccccccgt tccatgaatt cgcctacgaa 1920
gggctgaaga tcaggccgtc ggcaccatat aagactacag tagtaggagt ctttggggtt 1980
ccgggatcag gcaagtctgc tattattaag agcctcgtga ccaaacacga tctggtcacc 2040
agcggcaaga aggagaactg ccaggaaata gttaacgacg tgaagaagca ccgcgggaag 2100
gggacaagta gggaaaacag tgactccatc ctgctaaacg ggtgtcgtcg tgccgtggac 2160
atcctatatg tggacgaggc tttcgcttgc cattccggta ctctgctggc cctaattgct 2220
cttgttaaac ctcggagcaa agtggtgtta tgcggagacc ccaagcaatg cggattcttc 2280
aatatgatgc agcttaaggt gaacttcaac cacaacatct gcactgaagt atgtcataaa 2340
agtatatcca gacgttgcac gcgtccagtc acggccatcg tgtctacgtt gcactacgga 2400
ggcaagatgc gcacgaccaa cccgtgcaac aaacccataa tcatagacac cacaggacag 2460
accaagccca agccaggaga catcgtgtta acatgcttcc gaggctgggc aaagcagctg 2520
cagttggact accgtggaca cgaagtcatg acagcagcag catctcaggg cctcacccgc 2580
aaaggggtat acgccgtaag gcagaaggtg aatgaaaatc ccttgtatgc ccctgcgtcg 2640
gagcacgtga atgtactgct gacgcgcact gaggataggc tggtgtggaa aacgctggcc 2700
ggcgatccct ggattaaggt cctatcaaac attccacagg gtaactttac ggccacattg 2760
gaagaatggc aagaagaaca cgacaaaata atgaaggtga ttgaaggacc ggctgcgcct 2820
gtggacgcgt tccagaacaa agcgaacgtg tgttgggcga aaagcctggt gcctgtcctg 2880
gacactgccg gaatcagatt gacagcagag gagtggagca ccataattac agcatttaag 2940
gaggacagag cttactctcc agtggtggcc ttgaatgaaa tttgcaccaa gtactatgga 3000
gttgacctgg acagtggcct gttttctgcc ccgaaggtgt ccctgtatta cgagaacaac 3060
```

FIG.6C

```
cactgggata acagacctgg tggaaggatg tatggattca atgccgcaac agctgccagg 3120
ctggaagcta gacatacctt cctgaagggg cagtggcata cgggcaagca ggcagttatc 3180
gcagaaagaa aaatccaacc gctttctgtg ctggacaatg taattcctat caaccgcagg 3240
ctgccgcacg ccctggtggc tgagtacaag acggttaaag gcagtagggt tgagtggctg 3300
gtcaataaag taagagggta ccacgtcctg ctggtgagtg agtacaacct ggctttgcct 3360
cgacgcaggg tcacttggtt gtcaccgctg aatgtcacag gcgccgatag gtgctacgac 3420
ctaagtttag gactgccggc tgacgccggc aggttcgact tggtctttgt gaacattcac 3480
acggaattca gaatccacca ctaccagcag tgtgtcgacc acgccatgaa gctgcagatg 3540
cttgggggag atgcgctacg actgctaaaa cccggcggca tcttgatgag agcttacgga 3600
tacgccgata aaatcagcga agccgttgtt tcctccttaa gcagaaagtt ctcgtctgca 3660
agagtgttgc gcccggattg tgtcaccagc aatacagaag tgttcttgct gttctccaac 3720
tttgacaacg gaaagagacc ctctacgcta caccagatga ataccaagct gagtgccgtg 3780
tatgccggag aagccatgca cacggccggg tgtgcaccat cctacagagt taagagagca 3840
gacatagcca cgtgcacaga agcggctgtg gttaacgcag ctaacgcccg tggaactgta 3900
ggggatggcg tatgcagggc cgtggcgaag aaatggccgt cagcctttaa gggagcagca 3960
acaccagtgg gcacaattaa aacagtcatg tgcggctcgt accccgtcat ccacgctgta 4020
gcgcctaatt tctctgccac gactgaagcg gaaggggacc gcgaattggc cgctgtctac 4080
cgggcagtgg ccgccgaagt aaacagactg tcactgagca gcgtagccat cccgctgctg 4140
tccacaggag tgttcagcgg cggaagagat aggctgcagc aatccctcaa ccatctattc 4200
acagcaatgg acgccacgga cgctgacgtg accatctact gcagagacaa aagttgggag 4260
aagaaaatcc aggaagccat tgacatgagg acggctgtgg agttgctcaa tgatgacgtg 4320
gagctgacca cagacttggt gagagtgcac ccggacagca gcctggtggg tcgtaagggc 4380
tacagtacca ctgacgggtc gctgtactcg tactttgaag gtacgaaatt caaccaggct 4440
gctattgata tggcagagat actgacgttg tggcccagac tgcaagaggc aaacgaacag 4500
atatgcctat acgcgctggg cgaaacaatg gacaacatca gatccaaatg tccggtgaac 4560
gattccgatt catcaacacc tcccaggaca gtgccctgcc tgtgccgcta cgcaatgaca 4620
```

FIG.6D

```
gcagaacgga tcgcccgcct taggtcacac caagttaaaa gcatggtggt ttgctcatct 4680
tttcccctcc cgaaatacca tgtagatggg gtgcagaagg taaagtgcga gaaggttctc 4740
ctgttcgacc cgacggtacc ttcagtggtt agtccgcgga agtatgccgc atctacgacg 4800
gaccactcag atcggtcgtt acgagggttt gacttggact ggaccaccga ctcgtcttcc 4860
actgccagcg ataccatgtc gctacccagt ttgcagtcgt gtgacatcga ctcgatctac 4920
gagccaatgg ctcccatagt agtgacggct gacgtacacc ctgaacccgc aggcatcgcg 4980
gacctggcgg cagatgtgca ccctgaaccc gcagaccatg tggacctcga gaacccgatt 5040
cctccaccgc gcccgaagag agctgcatac cttgcctccc gcgcggcgga gcgaccggtg 5100
ccggcgccga gaaagccgac gcctgcccca aggactgcgt ttaggaacaa gctgcctttg 5160
acgttcggcg actttgacga gcacgaggtc gatgcgttgg cctccgggat tactttcgga 5220
gacttcgacg acgtcctgcg actaggccgc gcgggtgcat atattttctc ctcggacact 5280
ggcagcggac atttacaaca aaaatccgtt aggcagcaca atctccagtg cgcacaactg 5340
gatgcggtcc aggaggagaa aatgtacccg ccaaaattgg atactgagag ggagaagctg 5400
ttgctgctga aaatgcagat gcacccatcg gaggctaata agagtcgata ccagtctcgc 5460
aaagtggaga acatgaaagc cacggtggtg gacaggctca catcgggggc cagattgtac 5520
acgggagcgg acgtaggccg cataccaaca tacgcggttc ggtacccccg ccccgtgtac 5580
tcccctaccg tgatcgaaag attctcaagc cccgatgtag caatcgcagc gtgcaacgaa 5640
tacctatcca gaaattaccc aacagtggcg tcgtaccaga taacagatga atacgacgca 5700
tacttggaca tggttgacgg gtcggatagt tgcttggaca gagcgacatt ctgcccggcg 5760
aagctccggt gctacccgaa acatcatgcg taccaccagc cgactgtacg cagtgccgtc 5820
ccgtcaccct ttcagaacac actacagaac gtgctagcgg ccgccaccaa gagaaactgc 5880
aacgtcacgc aaatgcgaga actacccacc atggactcgg cagtgttcaa cgtggagtgc 5940
ttcaagcgct atgcctgctc cggagaatat tgggaagaat atgctaaaca acctatccgg 6000
ataaccactg agaacatcac tacctatgtg accaaattga aaggcccgaa agctgctgcc 6060
ttgttcgcta agacccacaa cttggttccg ctgcaggagg ttcccatgga cagattcacg 6120
gtcgacatga aacgagatgt caaagtcact ccagggacga aacacacaga ggaaagaccc 6180
```

FIG.6E

```
aaagtccagg taattcaagc agcggagcca ttggcgaccg cttacctgtg cggcatccac 6240
agggaattag taaggagact aaatgctgtg ttacgcccta acgtgcacac attgtttgat 6300
atgtcggccg aagactttga cgcgatcatc gcctctcact tccacccagg agacccggtt 6360
ctagagacgg acattgcatc attcgacaaa agccaggacg actccttggc tcttacaggt 6420
ttaatgatcc tcgaagatct aggggtggat cagtacctgc tggacttgat cgaggcagcc 6480
tttggggaaa tatccagctg tcacctacca actggcacgc gcttcaagtt cggagctatg 6540
atgaaatcgg gcatgtttct gactttgttt attaacactg ttttgaacat caccatagca 6600
agcagggtac tggagcagag actcactgac tccgcctgtg cggccttcat cggcgacgac 6660
aacatcgttc acggagtgat ctccgacaag ctgatggcgg agaggtgcgc gtcgtgggtc 6720
aacatggagg tgaagatcat tgacgctgtc atgggcgaaa aacccccata tttttgtggg 6780
ggattcatag tttttgacag cgtcacacag accgcctgcc gtgtttcaga cccacttaag 6840
cgcctgttca agttgggtaa gccgctaaca gctgaagaca agcaggacga agacaggcga 6900
cgagcactga gtgacgaggt tagcaagtgg ttccggacag gcttgggggc cgaactggag 6960
gtggcactaa catctaggta tgaggtagag ggctgcaaaa gtatcctcat agccatggcc 7020
accttggcga gggacattaa ggcgtttaag aaattgagag gacctgttat acacctctac 7080
ggcggtccta gattggtgcg ttaatacaca gaattctgat tggatcatag cgcactatta 7140
taggatccag atcccgggta attaattgaa ttacatccct acgcaaacgt tttacggccg 7200
ccggtggcgc ccgcgcccgg cggcccgtcc ttggccgttg caggccactc cggtggctcc 7260
cgtcgtcccc gacttccagg cccagcagat gcagcaactc atcagcgccg taaatgcgct 7320
gacaatgaga cagaacgcaa ttgctcctgc taggcctccc aaaccaaaga agaagaagac 7380
aaccaaacca aagccgaaaa cgcagcccaa gaagatcaac ggaaaaacgc agcagcaaaa 7440
gaagaaagac aagcaagccg acaagaagaa gaagaaaccc ggaaaaagag aaagaatgtg 7500
catgaagatt gaaaatgact gtatcttcgt atgcggctag ccacagtaac gtagtgtttc 7560
cagacatgtc gggcaccgca ctatcatggg tgcagaaaat ctcgggtggt ctgggggcct 7620
tcgcaatcgg cgctatcctg gtgctggttg tggtcacttg cattgggctc cgcagataag 7680
ttagggtagg caatggcatt gatatagcaa gaaaattgaa aacagaaaaa gttagggtaa 7740
```

FIG.6F

```
gcaatggcat ataaccataa ctgtataact tgtaacaaag cgcaacaaga cctgcgcaat 7800
tggccccgtg gtccgcctca cggaaactcg gggcaactca tattgacaca ttaattggca 7860
ataattggaa gcttacataa gcttaattcg acgaataatt ggatttttat tttattttgc 7920
aattggtttt taatatttcc aaaaaaaaaa aaaaaaaaaa aaaaaaaaaa aaaaaaaaaa 7980
aaaaaaaaaa aaaaaaaaaa aaaaaaaaaa ctagcgggtc ggcatggcat ctccacctcc 8040
tcgcggtccg acctgggcat ccgaaggagg acgcacgtcc actcggatgg ctaagggaga 8100
```

ALPHAVIRUS VECTORS FOR PARAMYXOVIRUS VACCINES

REFERENCE TO RELATED APPLICATIONS

This application is a United States National Phase filing under 35 USC 371 of PCT/CA98/01064 filed Nov. 13, 1998, which itself claims priority under 35 USC 119 from U.S. Provisional Patent Application No. 60/065,791 filed Nov. 14, 1997.

FIELD OF INVENTION

The present invention relates to the field of paramyxoviridae vaccines and is particularly concerned with vaccines comprising DNA encoding the fusion (F) protein of respiratory syncytial virus (RSV) in an alphavirus vector.

BACKGROUND OF THE INVENTION

Human respiratory syncytial virus (RSV) has been identified as a major pathogen responsible for severe respiratory tract infections in infants, young children and the institutionalized elderly (refs. 1, 2, 3, 4—throughout this application, various references are cited in parentheses to describe more fully the state of the art to which this invention pertains. Full bibliographic information for each citation is found at the end of the specification, immediately preceding the claims. The disclosures of these references are hereby incorporated by reference into the present disclosure). Global mortality and morbidity figures indicate that there is an urgent need for an efficacious RSV vaccine (refs. 5, 6). In the USA alone, approximately 100,000 children are hospitalized annually with severe cases of pneumonia and bronchiolitis resulting from an RSV infection. Inpatient and ambulatory care for children with RSV infections has been estimated to cost in excess of $340 million each year in the USA. The World Health Organization (WHO) and the National Institute of Allergy and Infectious Disease (NIAID) vaccine advisory committees have ranked RSV second only to HIV for vaccine development. Both the annual morbidity and mortality figures as well as the staggering health care costs for managing RSV infections have provided the incentive for aggressively pursuing the development of efficacious RSV vaccines. However, such a vaccine is still not available.

Formalin-inactivated (FI-RSV) and live attenuated RSV vaccines have failed to demonstrate efficacy in clinical trials (refs. 7, 8, 9, 10). Moreover, the formalin-inactivated RSV vaccine caused enhanced disease in some children following exposure to wild-type RSV (refs. 7, 8, 9, 10). Elucidation of the mechanism(s) involved in the potentiation of RSV disease is important for the design of safe RSV vaccines, especially for the seronegative population. Recent experimental evidence suggests that an imbalance in cell-mediated responses may contribute to immunopotentiation. Enhanced histopathology observed in mice that were immunized with the FI-RSV and challenged with virus could be abrogated by depletion of CD4+ cells or both interleukin-4 (IL-4) and IL-10.

The RSV fusion (F) glycoprotein is one of the major immunogenic proteins of the virus. This envelope glycoprotein mediates both fusion of the virus to the host cell membrane and cell-to-cell spread of the virus (ref. 1). The F protein is synthesized as a precursor ($F_0$) molecule which is proteolytically cleaved to form a disulphide-linked dimer composed of the N-terminal $F_2$ and C-terminal $F_1$ moieties (ref. 11). The amino acid sequence of the F protein is highly conserved among RSV subgroups A and B and is a cross-protective antigen (refs. 6, 12). In the baculovirus expression system, a truncated secreted version of the RSV F protein has been expressed in *Trichoplusia ni* insect cells (ref. 13). The recombinant protein was demonstrated to be protective in the cotton rats (ref. 13).

Studies on the development of live viral vaccines and glycoprotein subunit vaccines against parainfluenza virus infection are being pursued. Clinical trial results with a formalin-inactivated PIV types 1, 2, 3 vaccine demonstrated that this vaccine was not efficacious (refs. 14, 15, 16). Further development of chemically-inactivated vaccines was discontinued after clinical trials with a formalin-inactivated RSV vaccine demonstrated that not only was the vaccine not effective in preventing RSV infection but many of the vaccinees who later become infected with RSV suffered a more serious disease. Most of parainfluenza vaccine research has focused on candidate PIV-3 vaccines (ref. 17) with significantly less work being reported for PIV-1 and PIV-2. Recent approaches to PIV-3 vaccines have included the use of the closely related bovine parainfluenza virus type 3 and the generation of attenuated viruses by cold-adaptation of the virus (refs. 18, 19, 20, 21).

Another approach to parainfluenza virus type 3 vaccine development is a subunit approach focusing on the surface glycoproteins hemagglutinin-neuraminidase (HN) and the fusion (F) protein (refs. 22, 23, 24). The HN antigen, a typical type II glycoprotein, exhibits both haemagglutination and neuraminidase activities and is responsible for the attachment of the virus to sialic acid containing host cell receptors. The type I F glycoprotein mediates fusion of the viral envelope with the cell membrane as well as cell to cell spread of the virus. It has recently been demonstrated that both the HN and F glycoproteins are required for membrane fusion. The F glycoprotein is synthesized as an inactive precursor (F) which is proteolytically cleaved into disulfide-linked F2 and F1 moieties. While the HN and F proteins of PIV-1, -2 and -3 are structurally similar, they are antigenically distinct. Neutralizing antibodies against the HN and F proteins of one of PIV type are not cross-protective. Thus, an effective PIV subunit vaccine must contain the HN and F glycoproteins from the three different types of parainfluenza viruses. Antibody to either glycoprotein is neutralizing in vitro. A direct correlation has been observed between the level of neutralizing antibody titers and resistance to PIV-3 infections in infants. Native subunit vaccines for parainfluenza virus type 3 have investigated the protectiveness of the two surface glycoproteins. Typically, the glycoproteins are extracted from virus using non-ionic detergents and further purified using lectin affinity or immunoaffinity chromatographic methods. However, neither of these techniques may be entirely suitable for large scale production of vaccines under all circumstances. In small animal protection models (hamsters and cotton rats), immunization with the glycoproteins was demonstrated to prevent infection with live PIV-3 (refs. 25, 26, 27, 28, 29).

The HN and F glycoproteins of PIV-3 have also been produced using recombinant DNA technology. HN and F glycoproteins have been produced in insect cells using the baculovirus expression system and by use of vaccinia virus and adenovirus recombinants (refs. 30, 31, 32, 33, 34). In the baculovirus expression system, both full-length and truncated forms of the PIV-3 glycoproteins as well as a chimeric F-HN fusion protein have been expressed. The recombinant proteins have been demonstrated to be protective in small animal models (see WO91/00104, U.S. application Ser. No. 07/773,949 filed Nov. 29, 1991, assigned to the assignee hereof).

Semliki Forest virus (SFV) is a member of the Alphavirus genus in the Togaviridae family. The mature virus particle contains a single copy of a ssRNA genome with a positive polarity that is 5'-capped and 3'-polyadenylated. It functions as an mRNA and naked RNA can start an infection when introduced into cells. Upon infection/transfection, the 5' two-thirds of the genome is translated into a polyprotein that is processed into the four nonstructural proteins (nsP1 to 4) by self cleavage. Once the ns proteins have been synthesized they are responsible for replicating the plus-strand (42S) genome into full-length minus strands (ref. 14). These minus-strands then serve as templates for the synthesis of new plus-strand (42S) genomes and the 26S subgenomic mRNA (ref. 14). This subgenomic mRNA, which is colinear with the last one-third of the genome, encodes the SFV structural proteins.

In 1991 Liljestrom and Garoff (ref. 15) designed a series of expression vectors based on the SFV cDNA replicon. These vectors had the virus structural protein genes deleted to make the way for heterologous inserts, but preserved the nonstructural coding region for production of the nsPl to 4 replicase complex. Short 5' and 3' sequence elements required for RNA replication were also preserved. A polylinker site was inserted downstream from the 26S promoter followed by translation stop sites in all three frames. An SpeI site was inserted just after the 3' end of the SFV cDNA for linearization of the plasmid for use in vitro transcription reactions.

Injection of SFV RNA encoding a heterologous protein have been shown to result in the expression of the foreign protein and the induction of antibody in a number of studies (refs. 16, 17). The use of SFV RNA inoculation to express foreign proteins for the purpose of immunization would have several of the advantages associated with plasmid DNA immunization. For example, SFV RNA encoding a viral antigen may be introduced in the presence of antibody to that virus without a loss in potency due to neutralization by antibodies to the virus. Also, because the protein is expressed in vivo the protein should have the same conformation as the protein expressed by the virus itself. Therefore, concerns about conformational changes which could occur during protein purification leading to a loss in immunogenicity, protective epitopes and possibly immunopotentiation, could be avoided by plasmid DNA immunization.

In copending U.S. patent application Ser. No. 08/476,397 filed Jun. 7, 1995 (now U.S. Pat. No. 6,019,980), assigned to the assignee hereof and the disclosure of which is incorporated herein by reference (WO96/40945), there is described reference the use of plasmid vectors containing RSV F protein-encoding DNA for DNA immunization against RSV infection. In copending U.S. patent application Ser. No. 08/896,442 filed Jul. 18, 1997, assigned to the assignee hereof and the disclosure of which is incorporated herein by reference, there is described the use of plasmid vectors containing RSV G protein-encoding DNA for DNA immunization against RSV infection.

In my copending U.S. patent application Ser. No. 08/923,558, filed Sep. 4, 1997 (now U.S. Pat. No. 6,060,308), assigned to the assignee hereof and the disclosure of which is incorporated by reference, I describe a DNA vector using an alphavirus vector, including Semliki Forest virus vector, containing a DNA sequence encoding a paramyxovirus protein, specifically RSV-F, for making an RNA transcript for immunization.

In WO95/27044, the disclosure of which is incorporated herein by reference, there is described the use of alphavirus CDNA vectors based on cDNA complementary to the alphavirus RNA sequence. Once transcribed from the CDNA under transcriptional control of a heterologous promoter, the alphavirus RNA is able to self-replicate by means of its own replicase and thereby amplify the copy number of the transcribed recombinant RNA molecules.

Infection with RSV leads to serious disease. It would be useful and desirable to provide improved vectors for in vivo administration of immunogenic preparations, including vaccines, for protection against disease caused by RSV and other paramyxoviruses. In particular, it would be desirable to provide vaccines that are immunogenic and protective in humans, including seronegative infants, that do not cause disease enhancement (immunopotentiation).

SUMMARY OF THE INVENTION

The present invention provides novel immunogenic materials and immunization procedures based on such novel materials for immunizing against disease caused by respiratory syncytial virus. In particular, the present invention is directed towards the provision of DNA vaccines against disease caused by infection with paramyxoviridae.

In accordance with one aspect of the present invention, there is provided a vector, comprising a first DNA sequence which is complementary to at least part of an alphavirus RNA genome and having the complement of complete alphavirus RNA genome replication regions to permit in vivo replication; a second DNA sequence encoding a paramyxovirus protein or a protein fragment that generates antibodies that specifically react with the paramyxovirus protein, the second DNA sequence being inserted into a region of the first DNA sequence which is non-essential for replication; the first and second DNA sequences being under transcriptional control of a promoter; and a third DNA sequence located adjacent the second DNA sequence to enhance the immunoprotective ability of the paramyxovirus protein when expressed in vivo from the vector in a host.

The paramyxovirus protein may be selected from the group consisting of a parainfluenza virus (PIV) and a respiratory syncytial virus (RSV). The PIV protein may be from PIV-1, PIV-2, PIV-3 or PIV-4, particularly the HN and F glycoproteins of PIV-3. The RSV protein particularly may be the F or G glycoprotein of RSV.

The second DNA sequence may encode a full length RSV F protein, or may encode a RSV F protein lacking the transmembrane anchor and cytoplasmic tail. The lack of the coding region for the transmembrane anchor and cytoplasmic tail results in a secreted form of the RSV F protein. Alternatively, as described in the aforementioned U.S. patent application Ser. No. 08/896,500, the second DNA sequence may encode the full-length RSV-G protein or a truncated RSV G protein lacking a transmembrane region, resulting in a secreted form of the protein.

The alphavirus preferably is a Semliki Forest virus and the first DNA sequence is the Semliki Forest viral sequence contained in plasmid PSFVI.

The third nucleotide sequence may comprise a pair of splice sites to prevent aberrant mRNA splicing, in vivo, whereby substantially all transcribed mRNA from the vector upon administration encodes the RSV protein. Such third nucleotide sequence is preferably located between the first nucleotide sequence and the promoter sequence. Such third nucleotide sequence may be that of rabbit β-globin intron II, as shown in FIG. 8 of copending U.S. patent application Ser. No. 08/476,397 (WO 96/040945).

The promoter sequence may be an immediate early cytomegalovirus (CMV) promoter. The human cytomegalovirus Intron A sequence may be provided downstream of the promoter and upstream of the third nucleotide sequence.

A vector encoding the F protein and provided in accordance with one embodiment of the invention may be specifically pMP44, having the identifying characteristics shown in FIG. 1D.

The vectors provided herein may be used to immunize a host against RSV infection or disease by in vivo expression of RSV F protein or RSV G protein, which may lack a transmembrane region, or other paramyxovirus protein, following administration of the vectors. In accordance with a further aspect of the present invention, therefore, there is provided a method of immunizing a host against disease caused by infection with respiratory syncytial virus or other paramyxovirus, which comprises administering to the host an effective amount of a vector provided herein.

The present invention also includes a novel method of using a gene encoding an RSV F or G protein or a fragment of an RSV or G protein capable of generating antibodies which specifically react with RSV F or G protein to protect a host against disease caused by infection with respiratory syncytial virus, which comprises isolating the gene; operatively linking said gene to a DNA sequence which is complementary to at least part of an alphavirus RNA genome and having the complement of complete alphavirus RNA genome replication regions in a region of said DNA sequence which is non-essential for replication to form a vector wherein said gene and DNA sequence are under transcriptional control of a promoter; operatively linking the gene to an immunoprotection enhancing sequence to produce an enhanced immunoprotection by the RSV F or G protein in the host, preferably by introducing the immunoprotection enhancing sequence between the control sequence and the alphavirus sequence; and introducing the vector into the host. A corresponding procedure may be used for other paramyxoviridae.

In addition, the present invention includes a method of producing a vaccine for protection of a host against disease caused by infection with respiratory syncytial virus (RSV), which comprises isolating a first DNA sequence encoding an RSV or G protein, from which the transmembrane anchor and cytoplasmic tail may be absent; operatively linking said first DNA sequence to a second DNA sequence which is complementary to at least part of an alphavirus RNA genome and having the complete alphavirus genome replication regions in a region of said second DNA sequence which is non-essential for replication to form a vector wherein said first and second DNA sequences are under transcriptional control of a promoter; operatively linking the first nucleotide sequence to a third nucleotide sequence to enhance the immunoprotective ability of the RSV F or G protein when expressed in vivo from the vector in a host; and formulating the vector as a vaccine for in vivo administration. A corresponding procedure may be used for other paramyxoviridae.

The present invention further includes a vaccine for administration to a host, including a human host, produced by the method as well as immunogenic compositions comprising an immunoeffective amount of the vectors described herein.

BRIEF DESCRIPTION OF DRAWINGS

FIGS. 3A to 3J contain the nucleotide sequence of plasmid pMP44 (SEQ ID NO:1);

FIG. 5 shows the nucleotide sequence for a synthetic oligonucleotide coding for the hepatitis delta ribozyme (SEQ ID no; 2,3); and FIGS. 6A to 6F show the nucleotide sequence for the SFV EcoRV-SpeI fragment ligated to the ribozyme of FIG. 5 (SEQ ID no: 4).

GENERAL DESCRIPTION OF INVENTION

Figure 1A:
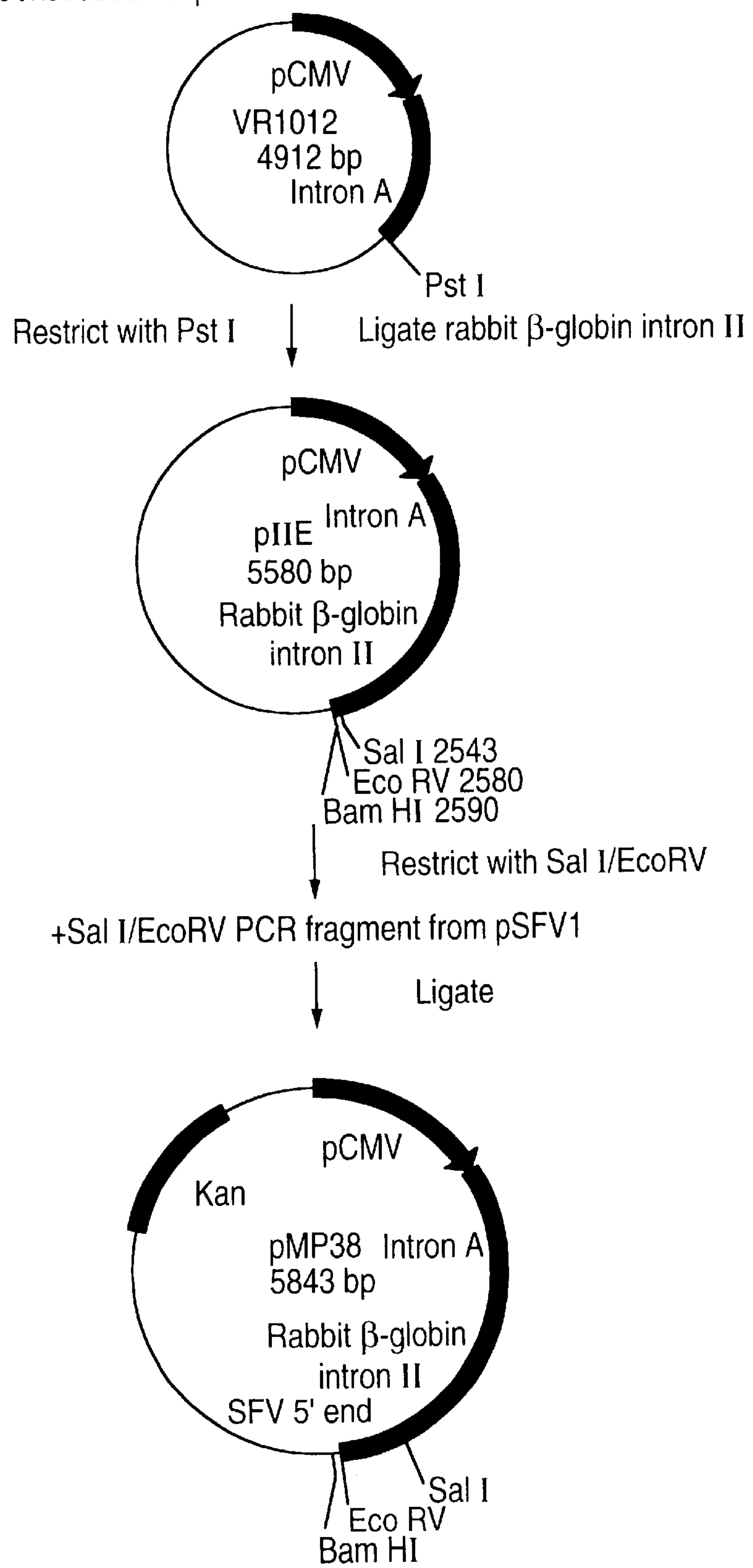
FIGS. 1A to 1B show a schematic of a procedure of assembly of vector pMP44.

As described above, the present invention, in general, relates to protection of hosts against disease caused by infection by paramyxovirus by DNA immunization using DNA vectors. In particular, the invention is concerned with protection of hosts against disease caused by infection by respiratory syncytial virus (RSV), although not specifically limited thereto. The description which follows refers specifically to employing DNA sequences encoding RSV F or G protein and fragments thereof which generate antibodies which specifically react with RSV F or G protein.

In this application, the terms "RSV F protein" and "RSV G protein" are used to define a full-length RSV F or G protein, including proteins having variations in their amino acid sequences including those naturally occurring in various strain of RSV and those introduced by PCR amplification of the encoding gene while retaining the immunogenic properties, a secreted form of the RSV F or G protein lacking a transmembrane anchor and cytoplasmic tail, as well as fragments capable of generating antibodies which specifically react with RSV F or G protein and functional analogs. In this application, a first protein is a "functional analog" of a second protein if the first protein is immunologically related to and/or has the same function as the second protein. The functional analog may be, for example, a fragment of the protein or a substitution, addition or deletion mutant thereof.

A vector is constructed to contain a first DNA sequence which is complementary to at least part of an alphavirus RNA genome, specifically Semliki Forest virus, and having the complement of complete alphavirus RNA genome replication regions to permit replication in vivo. A second DNA sequence encoding the RSV F or G protein is inserted into a region of the first DNA sequence which is non-essential for replication. The first and second DNA sequences are under transcriptional control of a promoter to permit expression of the RSV protein in a host immunized with the vector.

The promoter sequence may be the immediately early cytomegalovirus (CMV) promoter. This promoter is described in ref. 36. Any other convenient promoter may be used, including constitutive promoters, such as, Rous Sarcoma Virus LTRs, and inducible promoters, such as metallothionine promoter, and tissue specific promoters.

The recombinant vector may include a third nucleotide sequence located adjacent the alphavirus sequence to enhance the immunoprotective ability of the RSV F or G protein when expressed in vivo in a host. Such enhancement may be provided by increased in vivo expression, for example, by increased mRNA stability, enhanced transcription and/or translation. This additional sequence preferably is located between the promoter sequence and the alphavirus sequence.

This enhancement sequence may comprise a pair of splice sites to prevent aberrant mRNA splicing during transcription so that substantially all transcribed mRNA is intact alphavirus RNA encoding a gene of interest, for example, an RSV F protein. Specifically, rabbit β-globin Intron II sequence may provide such splice sites, as also described in ref. 37.

Additional enhancement may be obtained by, including an additional DNA sequence between the promoter and the enhancer sequence. Such additional DNA sequence may comprise the immediate early cytomegalovirus Intron A sequence.

The vectors provided herein, when administered to an animal, effect in vivo RSV F protein expression, as demonstrated by an antibody response in the animal to which it is administered and the conferring of protection. As may be seen from the results detailed in the Examples below, the DNA vectors produced a high anti-F IgG antibody titer and confer protection.

In comparison to the vectors described in the aforementioned U.S. patent application Ser. No. 08/476,397 (now U.S. Pat. No. 6,019,980) and Ser. No. 08/896,442, the vectors described herein provide a protective immune response using a lower dose and less time. In comparison to the vectors described in the aforementioned U.S. patent application Ser. No. 08/923,558 (now U.S. Pat. No. 6,060, 308), Ser Nos. 08/896,442 and 08/476,397 using native RSV F, the vectors described herein produce protective immune response in the absence of pretreatment of the animal model with cardiotoxin, a material known to increase the uptake of DNA and enhance the immune response.

The vector provided herein may also comprise a fourth nucleotide sequence encoding a further antigen from RSV, an antigen from at least one other pathogen or at least one immunomodulating agent, such as cytokine. Such vector may contain said fourth nucleotide sequence in a chimeric or a bicistronic structure. Alternatively, vectors containing the fourth nucleotide sequence may be separately constructed and coadministered to a host, with the DNA vector provided herein.

In addition, there may be provided at the 3'-end of the Simliki Forest virus segment, a hepatitis delta virus ribosyme sequence to ensure proper in vivo cleavage at the 3'-end of the Simliki Forest virus sequence. Any other convenient sequence may be employed to achieve this effect.

It is clearly apparent to one skilled in the art, that the various embodiments of the present invention have many applications in the fields of vaccination, diagnosis and treatment of RSV infections. A further non-limiting discussion of such uses is further presented below, 1. Vaccine Preparation and Use Immunogenic compositions, suitable to be used as vaccines, may be prepared from the RSV F or RSV G genes and other paramyxovirus genes and vectors as disclosed herein. The vaccine elicits an immune response in a subject which includes the production of anti-F or anti-G antibodies. Immunogenic compositions, including vaccines, containing the DNA vector may be prepared as injectables, in physiologically-acceptable liquid solutions or emulsions for polynucleotide administration. The nucleic acid may be associated with liposomes, such as lecithin liposomes or other liposomes known in the art, as a nucleic acid liposome (for example, as described in WO 93/24640, ref. 38) or the DNA vector may be associated with an adjuvant, as described in more detail below. Liposomes comprising cationic lipids interact spontaneously and rapidly with polyanions such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lysosomal compartment. Published PCT application WO 94/27435 describes compositions for genetic immunization comprising cationic lipids and polynucleotides. Agents which assist in the cellular uptake of nucleic acid, such as calcium ions, viral proteins and other transfection facilitating agents, may advantageously be used.

Polynucleotide immunogenic preparations may also be formulated as microcapsules, including biodegradable time-release particles. Thus, U.S. Pat. No. 5,151,264 describes a particulate carrier of a phospholipid/glycolipid/polysaccharide nature that has been termed Bio Vecteurs Supra Moleculaires (BVSM). The particulate carriers are intended to transport a variety of molecules having biological activity in one of the layers thereof.

U.S. Pat. No. 5,075,109 describes encapsulation of the antigens trinitrophenylated keyhole limpet hemocyanin and staphylococcal enterotoxin B in 50:50 poly (DL-lactideco-glycolide). Other polymers for encapsulation are suggested, such as poly(glycolide), poly(DL-lactide-co-glycolide), copolyoxalates, polycaprolactone, poly(lactide-co-caprolactone), poly(esteramides), polyorthoesters and poly (8-hydroxybutyric acid), and polyanhydrides.

Published PCT application WO 91/06282 describes a delivery vehicle comprising a plurality of bioadhesive microspheres and antigens. The microspheres being of starch, gelatin, dextran, collagen or albumin. This delivery vehicle is particularly intended for the uptake of vaccine across the nasal mucosa. The delivery vehicle may additionally contain an absorption enhancer.

The RSV F or G genes and vectors may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously, intravenously, intradermally or intramuscularly, possibly following pretreatment of the injection site with a local anaesthetic. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients, such as, for example, pharmaceutical grades of saccharine, cellulose and magnesium carbonate.

The immunogenic preparations and vaccines are administered in a manner compatible with the dosage formulation, and in such amount as will be therapeutically effective, protective and immunogenic. The quantity to be administered depends on the subject to be treated, including, for example, the capacity of the individualls immune system to synthesize the RSV F protein and antibodies thereto, and if needed, to produce a cell-mediated immune response. Precise amounts of active ingredient required to be administered depend on the judgment of the practitioner. However, suitable dosage ranges are readily determinable by one skilled in the art and may be of the order of about 1 $\mu$g to about 1 mg of the RSV F or G genes and vectors. Suitable regimes for initial administration and booster doses are also variable, but may include an initial administration followed by subsequent administrations. The dosage may also depend on the route of administration and will vary according to the size of the host. A vaccine which protects against only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

In particular embodiments of the present invention, the vector comprising a first nucleotide sequence encoding an F or G protein of RSV may be delivered in conjunction with a targeting molecule to target the vector to selected cells including cells of the immune system.

The DNA vectors may be delivered to the host by a variety of procedures, for example, Tang et al. (ref. 39) disclosed that introduction of gold microprojectiles coated with DNA encoding bovine growth hormone (BGH) into the skin of mice resulted in production of anti-BGH antibodies in the mice, while Furth et al. (ref. 40) showed that a jet injector could be used to transfect skin, muscle, fat and mammary tissues of living animals.

2. Immunoassays

The RSV F or G genes and vectors of the present invention are useful as immunogens for the generation of anti-F or anti-G antibodies for use in immunoassays, including enzyme-linked immunosorbent assays (ELISA), RIAs and other non-enzyme linked antibody binding assays or procedures known in the art. In ELISA assays, the vector first is administered to a host to generate antibodies specific to the RSV F or G protein or other paramyxovirus protein. These RSV F- or G-specific antibodies are immobilized onto a selected surface, for example, a surface capable of binding the antibodies, such as the wells of a polystyrene microtiter plate. After washing to remove incompletely adsorbed antibodies, a nonspecific protein such as a solution of bovine serum albumin (BSA) that is known to be antigenically neutral with regard to the test sample may be bound to the selected surface. This allows for locking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This procedure may include diluting the sample with diluents, such as solutions of BSA, bovine gamma globulin (BGG) and/or phosphate buffered saline (PBS)/Tween. The sample is then allowed to incubate for from about 2 to 4 hours, at temperatures such as of the order of about 20° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound RSV F specific antibodies, and subsequent washing, the occurrence, and even amount, of immunocomplex formation may be determined.

Bioloical Deposits

Certain vectors that contain the gene encoding RSV F protein and referred to herein have been deposited with the American Type Culture Collection (ATCC) located at 10801 University Boulevard, Manassas, Va. 20110-2209, U.S.A., pursuant to the Budapest Treaty and prior to the filing of this application.

Samples of the deposited plasmids will become available to the public upon grant of a patent based upon this United States patent application and all restrictions on access to the deposits will be removed at that time. Non-viable deposits will be replaced. The invention described and claimed herein is not to be limited in scope by plasmids deposited, since the deposited embodiment is intended only as an illustration of the invention. Any equivalent or similar plasmids that encode similar or equivalent antigens as described in this application are within the scope of this invention.

Deposit Summary

| Plasmid | ATCC Designation | Date Deposited |
|---|---|---|
| pMP37<br>pMP42 | 97905 | Feb. 27, 1997 |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry and immunology used but not explicitly described in this disclosure and these Examples are amply reported in the scientific literature and are well within the ability of those skilled in the art.

Example 1

Figure 1B:
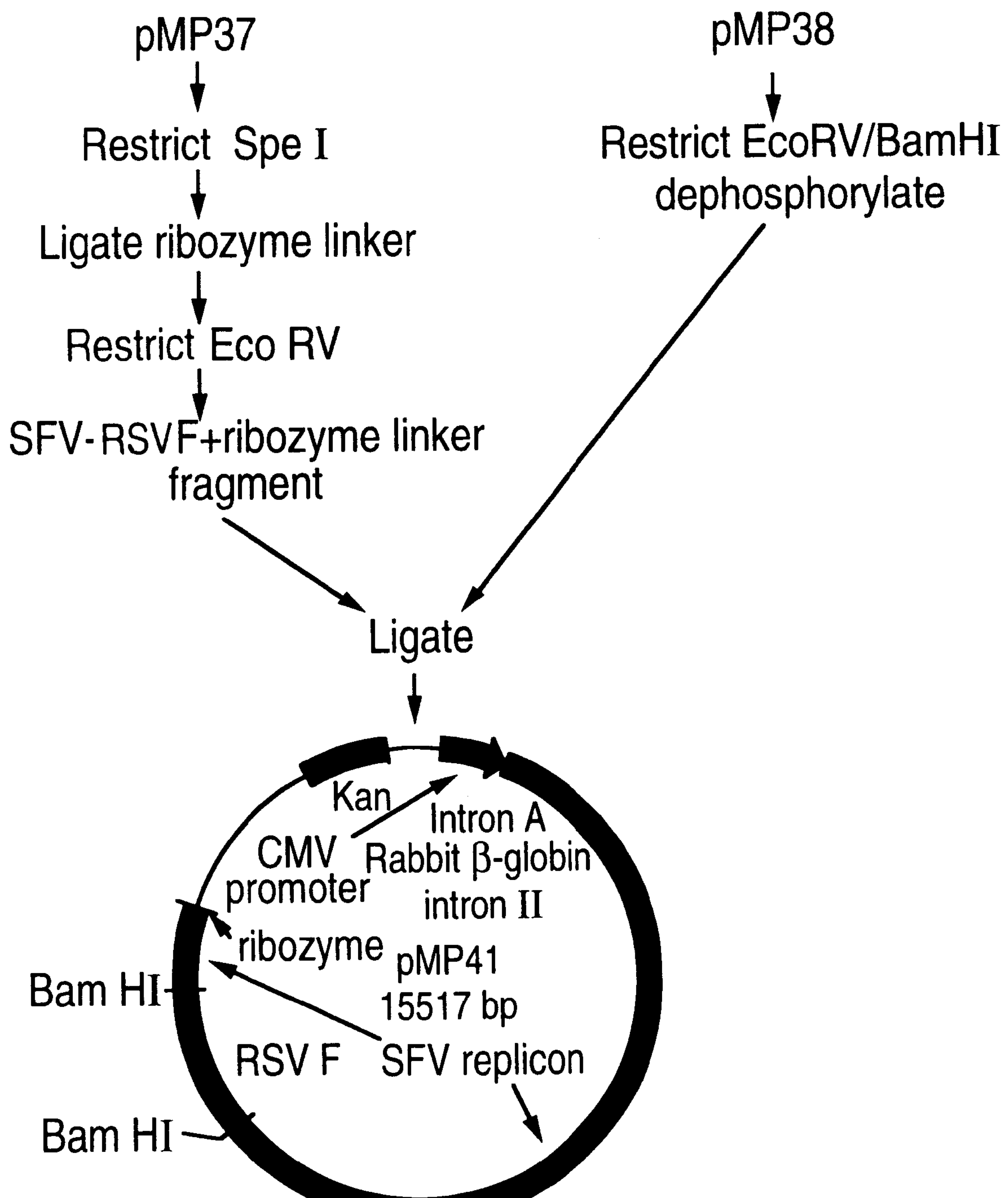

This Example describes a scheme for construction of a Semliki Forest Virus (SFV) DNA expression vector containing a truncated RSV F gene as outlined in FIGS. 1A to 1B.

Plasmid VR1012 was restricted with PstI and then made blunt-ended with T4 DNA polymerase. The β-globin Intron II was exised out of vector pSG5 (Stratagene) and ligated into plasmid VR1012 to generate plasmid pIIE. Plasmid pIIE was then restricted with SaII and EcoRV and ligated to a PCR fragment having the nucleotide sequence: TCGACATGGCGGATGTGTGACATACACGACGCCAAAAGATTTTGTTCCAGCTCCTGCCACCTCCGCTACGCGAGAGATTAACCACCCACGATGGCCGCCAAAGTGCATGTTGATATTGAGGCTGACAGCCCATTCATCAAGTCTTTGCAGMGGCATTTCCGTCGTTCGAGGTGGAGTCATTGCAGGTCACAGCAAATGACCATGCAAATGCCAGAGCATTTTCGCACCTGGCTACCAAATTGATCGAGCAGGAGACTGACAAAGACACACTCATCTTGGAT (SEQ ID no: 7) generated from pSFVI with primers SAL-SFV having the nucleotide sequence 5'-TCCACCTCCAAGAT ATCCAAGATGAGTGTG (SEQ ID no: 5) and ECO-SFV having the nucleotide sequence 5'-TCCACCTCCAAGAT ATCCAAGATGAGTGTG (SEQ ID no: 6). The resulting plasmid pMP38 was then restricted with EcoRV and BamHI and then dephosphorylated. Plasmid pSFV1 link (see copending U.S. patent application Ser. No. 09/190,245 filed Nov. 13, 1998) was then restricted with SpeI and ligated to the hepatitis delta ribozyme (FIG. 5, SEQ ID nos: 2 and 3). The ligation reaction was then restricted with EcoRV to release most of the SFV-RSVF plus ribozyme fragment. This fragment was then ligated to EcoRV/BamH1 restricted pMP38 to produce pMP41.

Example 2

Figure 2A:
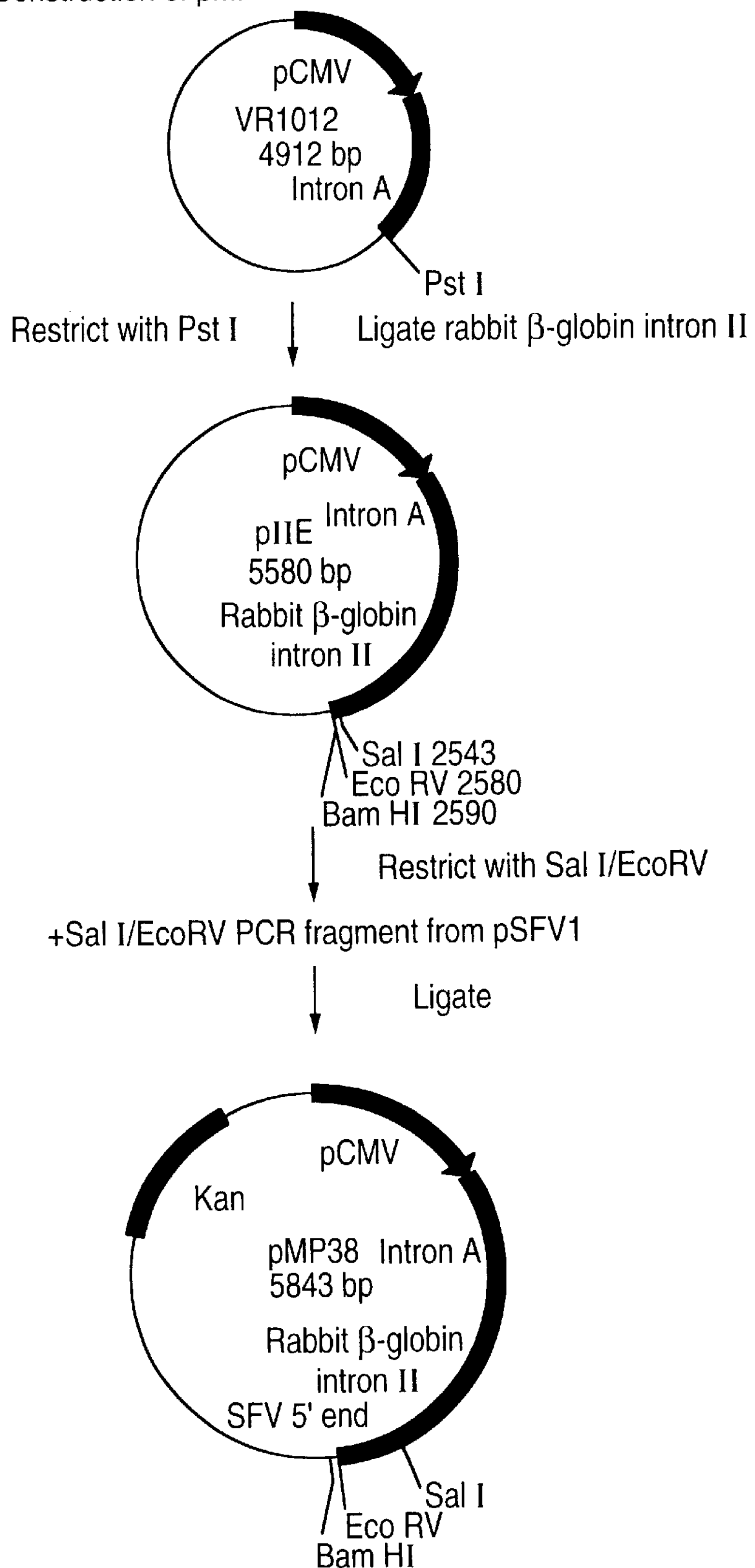
FIGS. 2A to 2B show a schematic of a procedure of assembly of vector pMP44.
Figure 2B:
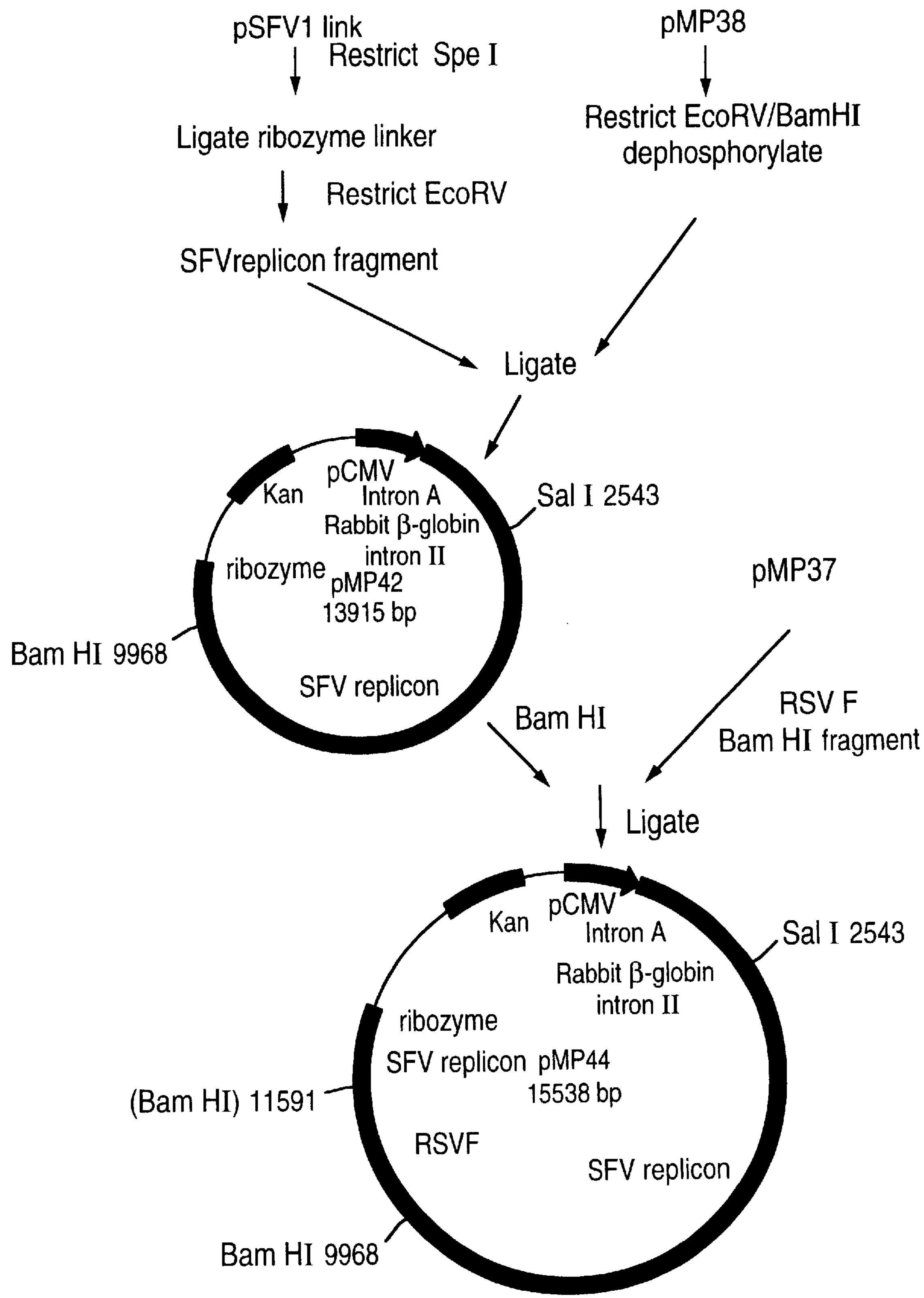

This Example describes an alternative scheme for constructing plasmid pMp44 as outlined in FIG. 2.

Plasmid VR1012 was restricted with PstI and then made blunt-ended with T4 DNA polymerase. The β-globin Intron II was exised out of vector pSG5 (Stratagene) and ligated into plasmid VR1012 to generate plasmid pIIE. Plasmid pIIE was then restricted with SaII and EcoRV and ligated to a PCR fragment having the nucleotide sequence:TCGACATGGCGGATGTGTGACATACACGACGCCAAAAGATTTTGTTCCAGCTCCTGCCACCTCCGCTACGCGAGAGATTAACCACCCACGATGGCCGCCAAAGTGCATGTTGATATTGAGGCTGACAGCCCATTCATCAAGTCTTTGCAGAAGGCATTTCCGTCGTTCGAGGTGGAGTCATTGCAGGTCACACCAAATGACCATGCAAATGCCAGAGCATTTTCGCACCTGGCTACCAAATTGATCGAGCAGGAGACTGACAAAGACACACTCATCTTGGAT (SEQ ID no: 7) generated from pSFVI with primers SAL-SFV having the nucleotide sequence 5'-TCCACCTCCAAGATATCCAAGATGAGTGTG (SEQ ID no: 5) and ECO-SFV having the nucleotide sequence 5'-TCCACCTCCAAGATATCCAAGATGAGTGTG (SEQ ID no: 6). The resulting plasmid pMP38 was then restricted with EcoRV and BamHI and then dephosphorylated. Plasmid pSFV1 link (see copending U.S. patent application Ser. No. 09/190,245 filed Nov. 13, 1998) was then restricted with SpeI and ligated to the hepatitis delta ribozyme (FIG. 5, SEQ ID nos: 2 and 3).

The ligation reaction product was then restricted with EcoRV to release the SFV replicon plus the ribozyme having the nucleotide sequence as outlines in FIGS. 6A to 6C. This fragment was then ligated to the EcoRV/BamHI restricted pMP38 to produce pMP42. The RSV F gene fragment was released from pMP37 by restriction with BamHI, and this fragment was ligated into the BamHI site of pMP42 to produce pMP44. The nucleotide sequence of pMP44 is shown in FIGS. 3A to 3E.

Example 3

This Example describes the immunization of mice with pMP44 and the immunogenicity results obtained.

BALB/C mice were immunized with plasmid pMP44 by the intramuscular (i.m.) route. The anterior tibialts muscles of six BALB/C mice were bilaterally injected with 2×100 μg of plasmid pMP44. This amount is equivalent to approximately 94 μg of a conventional vector, based on copy number. These mice were boosted in an identical manner 4 weeks later. The control group was immunized with 2×25 μg of SFV-RSV F RNA as described in my aforementioned U.S. application Ser. No. 08/923,558 (now U.S. Pat. No. 6,060,308), except that the muscles were not pre-treated with cardiotoxin. SFV-RSV F DNA was prepared by linearizing pMP37 (ATCC 97905) by culturing with SpeI. The immunization protocol is set forth in the following Table I:

TABLE 1

| | Immunization protocol | | | |
|---|---|---|---|---|
| Group | Prime | Route of Inoculation | Boost | Route of Inoculation |
| 1 | SFV-RSVF RNA[1] | Intramuscular | SFV-RSVF RNA[1] | Intramuscular |
| 2 | pMP44 DNA[2] | Intramuscular | pMP44DNA[2] | Intramuscular |

Mice were Inoculated With 1. 25 μg of RNA was injected into each hind leg muscle in 50 μL of PBS
2. 100 μg of DNA was injected into each hind leg muscle in 50 μL of PBS Sera was obtained from the mice at 4 and 6 weeks. Anti-RSV F antibody titers (IgG) in these sera were determined by enzyme-linked immunosorbent assay (ELISA), as described in Example 3.

Figure 4:
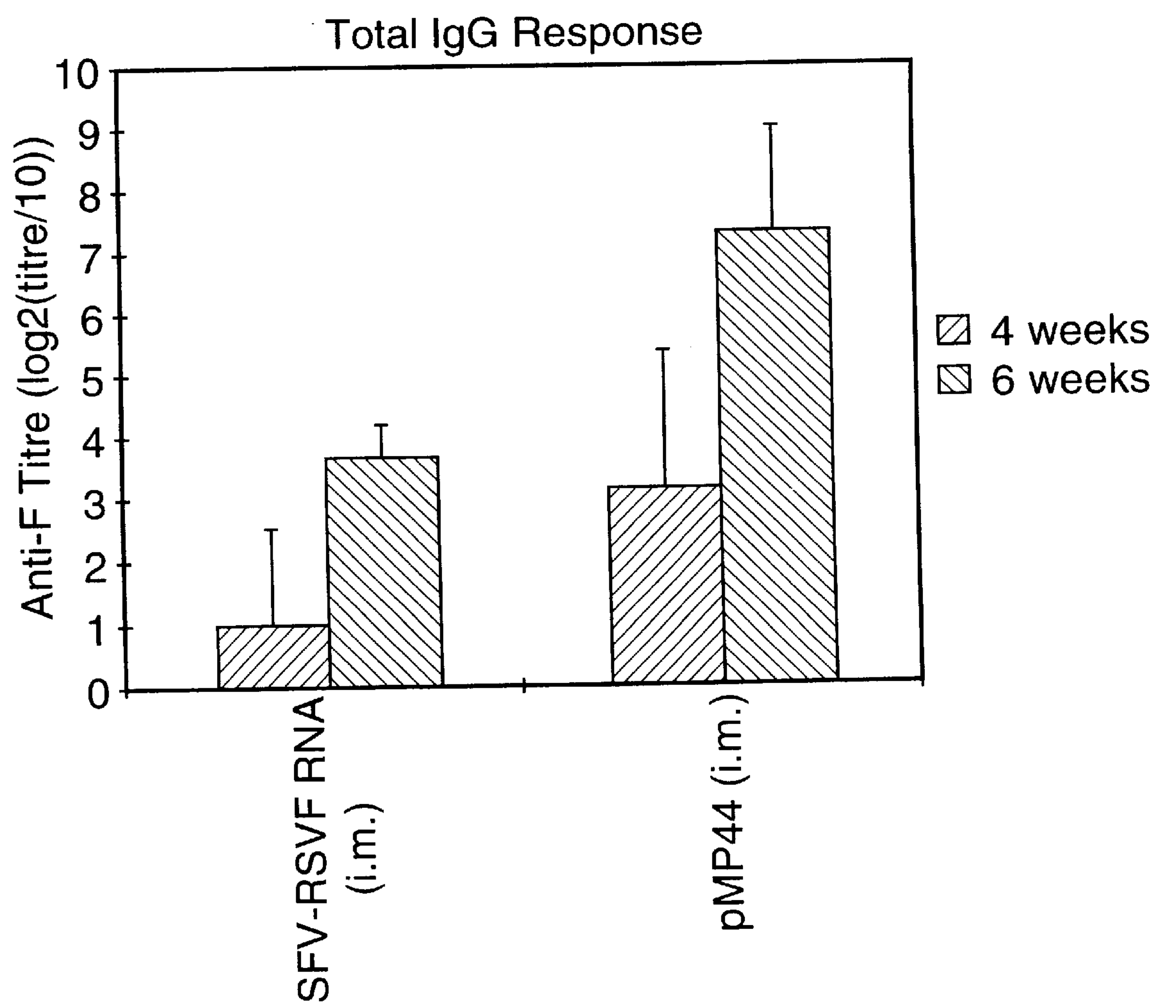
FIG. 4 shows the anti-RSV F titers in sera from mice taken 4 weeks after priming and 2 weeks after boosting.

The anti-RSV F IgG antibody response in the sera of the BALB/C mice are summarized in FIG. 4. The mice immunized with the DNA construct, pMP44, had higher anti-F titers than the mice immunized with the SFV-RSV F RNA.

Two weeks after the second immunization, mice were challenged intranasally with $10^6$ plaque forming units (pfu) of the A1 strain of RSV (BG-4A). Animals were sacrificed 4 days later. Lungs were asceptically removed, weighed, and homogenized in 2 mL of complete culture medium. The virus titer in lung homogenates was determined in duplicate using vero cells, as previously described (ref. 41).

As seen in Table 2 below, immunization of mice with pMP44 DNA protected mice (5/6) against live RSV challenge, in contrast to the lack of protection when immunization with SFV-RSV F RNA was effected. This result contrasts with the complete protection which is obtained using SFV-RSV F RNA as described in U.S. patent application Ser. No. 08/923,558, where the results show protection after pretreatment with cardiotoxin. In U.S. patent application Ser. No: 08/476,397 (now U.S. Pat. No. 6,019, 980), complete protection was obtained with plasmid pXL2 (ATCC 97168) after pretreatment with cardiotoxin. In U.S. patent application Ser. No. 08/476,442, complete protection was obtained with plasmids pXL5 and pXL6 after pretreatment with cardiotoxin. In each case, pretreatment with cardiotoxin was effected by injecting 2×50 μL of cardiotoxin in 10 μM of PBS in the anterior tibialts muscles 5 days prior to injection of the nucleic acid constructs.

TABLE 2

| | Immunogen | | Mean Virus Lung Titre | |
|---|---|---|---|---|
| Group | Prime | Boost | (log10/g ± s.d) | % Protection |
| 1 | SFV-RSVF RNA | SFV-RSVF RNA | 4.26 | 0 |
| 2 | pMP44 DNA | pMP44DNA | 2.12* | 83 |

*Limit of detection = 1.8

Example 4

This Example describes the determination of anti-RSV F antibody titers.

Nunc-MaxiSorp plate wells were coated overnight at room temperature with 2.5 ng of immunoaffinity-purified RSV F protein diluted in 0.05M carbonate-bicarbonate buffer, pH 9.6. Wells were blocked for non-specific binding by adding 0.1% BSA in PBS for 30 min. at room temperature, followed by two washes in a washing buffer of 0.1% BSA in PBS+0.1% Tween 20. Serial two or four-fold dilutions of mouse serum was added to the wells. After a one hour incubation at room temperature, plates were washed five times with washing buffer, and horseradish peroxidase (HRP) labeled conjugate was added at the appropriate optimal dilution in washing buffer. The total IgG assay used $F(ab')_2$ goat antimouse IgG (H+L specific)—HRP from Jackson Immuno Research Laboratory Inc. (Baltimore, Md., USA). Sheep anti-mouse IgG1-HRP from Serotec (Toronto, Ontario, Canada) was used in the IgG1 assay and goat anti-mouse IgG2a from Caltag Laboratories (San Francisco, Calif., USA) was used in the IgG2a assay. Following one hour incubation at room temperature, the plates were washed five times with washing buffer, and hydrogen peroxide (substrate) in the presence of tetramethylbenzidine was added. The reaction was stopped by adding 2 M sulfuric acid. The colour was read in a Multiscan Titertek plate reader at an optical density (OD) of 450 nm. The titer was taken as the reciprocal of the last dilution at which the OD was approximately double. This OD must be greater than the negative control of the assay at the starting dilution. The pre-immune serum of each animal was used as the negative control.

SUMMARY OF THE DISCLOSURE

In summary of this disclosure, the present invention provides certain novel alphavirus derived DNA vectors containing genes encoding RSV F or RSV G proteins, or other paramyxovirus proteins, methods of immunization using such vectors and methods of diagnosis using such vectors. Modifications are possible within the scope of this invention.

REFERENCES

1. McIntosh K. and Chanock R. M. in Fields B. N. and Knipe D. M. (eds). Virology. Raven Press, New York, 1990, pp.1045–1072.
2. Murphy B. R., Hall S. L., Kulkarni A. B., Crowe J. E., Collins P. L., Connors M., Karron R. A. and Chanock R. M., Virus Res 32, 13–36, 1994.
3. Osterweil D. and Norman D., Am Geriat Soc 36, 659–662, 1990.
4. Agius G., Dindinand G., Biggar R. J., Peyre R., Vaillant V., Ranger S., Poupet J. Y., Cisse M. F. and Casters M., J Med Virol 30, 117–127, 1990.
5. Katz S. L. in New vaccine development establishing priorities Vol 1. National Academic Press, Washington, 1985, pp. 3974 09.
6. Wertz G. W. and Sullender W. M., Biotechnology 20, 151–176, 1992.
7. Fulginiti V. A., Eller J. J., Sieber O. F., Joyner J. W., Minamitani M. and Meiklejohn G., Am i Epidemiol 89, 449–463, 1969.
8. Chin J., Magoffin R. L., Shearer I. A., Schieble J. H. and Lennette E. H., Am J Epidemiol 89, 449–463, 1969.
9. Belshe R. B., Van Voris L. P. and Mufson M. A., J Infect Dis 145, 311–319, 1982.
10. Kim R. M., Arrobio J. O., Pyles G., Brandt C. D., Camargo E., Chanock R. M. and Parrott R. H., Pediatrics 48, 745–755, 1971.
11. Gruber C. and Levine S., J Gen Virol 64, 825–832, 1983.
12. Olmstead R. A., Elango N. and Prince G. A., Proc Natl Acad Sci USA 83, 7462–7466, 1991.
13. Parrington M., Cockle S., Wyde P., Du R.-P., Snell E., Yan W.-Y., Wang Q., Gisonni L., Sanhueza S., Ewasyshyn M. and Klein M., Virus Genes 14, 65–74, 1997
14. Fulginiti, V. A., Eller, J. J., Sieber, O. F., Joyner, J. W., Minamitani, M. and Meiklejohn, G. (1969) Am. J. Epidemiol. 89 (4), 435–448.
15. Chin, J., Magoffin, R. L., Shearer, L. A., Schieble, J. H. and Lennette, E. H. (1969) Am. J. Epidemiol. 89 (4), 449–463.
16. Jensen, K. E., Peeler, B. E. and Dulworth, W. G. (1962) J. Immunol. 89, 216–226.
17. Murphy, B. R., Prince, G. A., Collins, P. L., Van Wyke -Coelingh, K., Olmsted, R. A., Spriggs, M. K., Parrott, R. H., Kim, H.-Y., Brandt, C. D. and Chanock, R. M. (1988) Vir. Res. 11, 1–15.
18. Hall, S. L., Sarris, C. M., Tierney, E. L., London, W. T., and Murphy, B. R. (1993) J. Infect. Dis. 167, 958–962.
19. Belshe, R. B., Karron, R. A., Newman, F. K., Anderson, E. L., Nugent, S. L., Steinhoff, M., Clements, M. L., Wilson, M. H., Hall, S. L., Tierney, E. L. and Murphy, B. R. (1992) J. Clin. Microbiol. 30 (8), 2064–2070.
20. Hall, S. L., Stokes, A., Tierney, E. L., London, W. T., Belshe, R. B., Newman, F. C. and Murphy, B. R. (1992) Vir. Res. 22, 173–184.
21. Van Wyke Coelingh, K. L., Winter, C. C., Tierney, E. L., London, W. T. and Murphy, B. R. (1988) J. Infect. Dis. 157 (4), 655–662.
22. Ray, R., Novak, M., Duncan, J. D., Matsuoka, Y. and Compans, R. W. (1993) J. Infect. Dis. 167, 752–755.
23. Ray, R., Brown, V. E. and Compans, R. W. (1985) J. Infect. Dis. 152 (6), 1219–1230.
24. Ray, R. and Compans, R. W. (1987) J. Gen. Virol. 68, 409–418.
25. Ray, R., Glaze, B. J., Moldoveanu, Z. and Compans, R. W. (1988) J. Infect. Dis. 157 (4), 648–654.
26. Ray, R., Watsuoka, Y., Burnett, T. L., Glaze, B. J. and Compans, R. W. (1990) J. Infect. Dis. 162, 746–749.
27. Ray, R., Glaze, B. J. and Compans, R. W. (1988) J. Virol. 62 (3), 783–787.
28. Ewasyshyn, M., Caplan, B., Bonneau A.-M., Scollard, N., Graham, S., Usman, S. and Klein, M. (1992) Vaccine 10 (6) , 412–420.
29. Ambrose, M. W., Wyde, P. R., Ewasyshyn, M., Bonneau, A.-M., Caplan, B., Meyer, H. L. and Klein, M. (1991) Vaccine 9, 505–511.
30. Kasel, J. A., Frank, A. L., Keitel, W. H., Taber, L. H., Glezen W. P. J. Virol. 1984; 52:828–32.
31. Lehman, D. J., Roof, L. L., Brideau, R. J., Aeed, P. A., Thomsen, D. R., Elhammer, A. P., Wathen, M. W. and Homa, F. L. (1993) J. Gen. Virol. 74, 459–469.
32. Brideau, R. J., Oien, N. L., Lehman, D. J., Homa, F. L. and Wathen, M. W. (1993) J. Gen. Virol. 74, 471–477.
33. Ebata, S. N., Prevec, L., Graham, F. L. and Dimock, K. (1992) Vir. Res. 24, 21–33.

34. Hall, S. L., Murphy, B. R. and Van Wyke Coelingh, K. L. (1991) Vaccine 9, 659–667.

35. Strauss E. G. and Strauss J. H., in Schlesinger S. S. and Schlesinger M. i. (eds). The Togaviridae and Flaviviridae. Plenum Press, New York, 1986, pp.35–90.

36. Chapman, B. S.; Thayer, R. M.; Vincent, K. A. and Haigwood, N. L., Nucl. Acids. Res. 1991, 19: 3979–3986.

37. Breathnack, R. and Harris, B. A., Nucl. Acids Res. 1983, 11: 7119–7136

38. Nabel, G. J. 1993, Proc. Natl. Acad. Sci USA 90: 11307–11311.

39. Tang et al., Nature 1992, 356: 152–154

40. Furth et al. Analytical Biochemistry, 1992, 205: 365–368

41. Prince, G. A. et al, Am. J. Pathol. 93, 771 to 790, 1978.

What we claim is:

1. A vector, comprising:

a first DNA sequence which is complementary to at least part of an alphavirus RNA genome and having the complement of complete alphavirus RNA genome replication regions to permit in vivo replication;

a second DNA sequence encoding a paramyxovirus protein or a protein fragment that elicits the generation of antibodies that specifically react with the paramyxovirus protein, the second DNA sequence being inserted into a region of the first DNA sequence which is non-essential for replication, the first and second DNA sequences being under transcriptional control of a promoter;

a third nucleotide sequence located between the first nucleotide sequence and the promoter sequence and comprising a pair of splice sites to prevent aberrant mRNA splicing; and a fourth nucleotide sequence which is a hepatitis delta virus ribozyme sequence at the 3'-end of the first nucleotide sequence to ensure proper in vivo cleavage at the 3'-end of the first nucleotide sequence.

2. The vector of claim 1 wherein the paramyxovirus protein is selected from the group consisting of a parainfluenza virus (PIV) and a respiratory syncytial virus (RSV).

3. The vector of claim 2 wherein the PIV protein is seletected from the group consisting of PIV-1, PIV-2, PIV-3 and PIV-4.

4. The vector of claim 3 wherein said PIV protein is selected from the group consisting of the HN and F glycoproteins of PIV-3.

5. The vector of claim 4 wherein the RSV protein is selected from the group consisting of the F or G glycoprotein of RSV.

6. The vector of claim 1 wherein the second DNA sequence encodes a full length RSV F or RSV G protein.

7. The vector of claim 1, wherein the second nucleotide sequence encodes a truncated RSV F or RSV G protein lacking the transmembrane anchor and cytoplasmic tail.

8. The vector of claim 1 wherein the alphavirus is a Semliki Forest virus.

9. The vector of claim 1 wherein the first DNA sequence is the Semliki Forest viral sequence contained in plasmid pSFVI.

10. The vector of claim 1 wherein the promoter sequence is an immediate early cytomegalovirus (CMV) promoter.

11. The vector of claim 1 wherein said third nucleotide sequence is that of rabbit β-globin intron II.

12. The vector of claim 1 wherein said promoter sequence is an immediate early cytomegalovirus (CMV) promoter and the human cytomegalovirus Intron A sequence is provided downstream of the promoter and upstream of the third nucleotide sequence.

13. The vector of claim 1 which is plasmid pMP44 shown in FIG. 2D.

14. The vector of claim 1 which consists of SEQ ID No: 1.

15. A method of producing a vaccine for protection of a host against disease caused by infection with respiratory syncial virus (RSV), which comprises:

isolating a first DNA sequence encoding an RSV F or G protein, from which the transmembrane anchor and cytoplasmic tail may be absent;

operatively linking said first DNA sequence to a second DNA sequence which is complementary to at least part of an alphavirus RNA genome and having the complete alphavirus genome replication regions in a region of said second DNA sequence which is non-essential for replication to form a vector wherein said first and second DNA sequences are under transcriptional control of a promoter;

inserting a third DNA sequence into the vector between the first DNA sequence and the second DNA sequence, said third DNA sequence comprising a pair of splice sites to prevent aberrant mRNA splicing:

locating a fourth nucleotide sequence which is a hepatitis delta virus ribozyme sequence in the vector at the 3'-end of the first DNA sequence to ensure proper in vivo cleavage at the 3'-end of the first DNA sequence; and formulating the vector as a vaccine for in vivo administration.

16. The method of claim 15 wherein said vector is pMP44 shown in FIG. 2D.

17. The method of claim 15 wherein said vector consists of SEQ ID no: 1.

* * * * *

SEQUENCE LISTING

<160> NUMBER OF SEQ ID NOS: 7

<210> SEQ ID NO 1
<211> LENGTH: 15538
<212> TYPE: DNA
<213> ORGANISM: respiratory syncytial virus

<400> SEQUENCE: 1

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg gggcctatac acccccgctt ccttatgcta   1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
```

-continued

```
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
cgatcctgag aacttcaggg tgagtttggg gacccttgat tgttctttct ttttcgctat   1920
tgtaaaattc atgttatatg gagggggcaa agttttcagg gtgttgttta gaatgggaag   1980
atgtcccttg tatcaccatg gaccctcatg ataattttgt ttctttcact ttctactctg   2040
ttgacaacca ttgtctcctc ttattttctt ttcatttttct gtaacttttt cgttaaactt   2100
tagcttgcat ttgtaacgaa tttttaaatt cacttttgtt tatttgtcag attgtaagta   2160
ctttctctaa tcactttttt ttcaaggcaa tcagggtata ttatattgta cttcagcaca   2220
gttttagaga acaattgtta taattaaatg ataaggtaga atatttctgc atataaattc   2280
tggctggcgt ggaaatattc ttattggtag aaacaactac atcctggtca tcatcctgcc   2340
tttctcttta tggttacaat gatatacact gtttgagatg aggataaaat actctgagtc   2400
caaaccgggc ccctctgcta accatgttca tgccttcttc tttttcctac agctcctggg   2460
caacgtgctg gttattgtgc tgtctcatca ttttggcaaa gaattgtaat acgactcact   2520
atagggcgaa ttgtcaccgt cgtcgacatg gcggatgtgt gacatacacg acgccaaaag   2580
attttgttcc agctcctgcc acctccgcta cgcgagagat taaccaccca cgatggccgc   2640
caaagtgcat gttgatattg aggctgacag cccattcatc aagtctttgc agaaggcatt   2700
tccgtcgttc gaggtggagt cattgcaggt cacaccaaat gaccatgcaa atgccagagc   2760
attttcgcac ctggctacca aattgatcga gcaggagact gacaaagaca cactcatctt   2820
ggatatcggc agtgcgcctt ccaggagaat gatgtctacg cacaaatacc actgcgtatg   2880
ccctatgcgc agcgcagaag accccgaaag gctcgatagc tacgcaaaga aactggcagc   2940
ggcctccggg aaggtgctgg atagagagat cgcaggaaaa atcaccgacc tgcagaccgt   3000
catggctacg ccagacgctg aatctcctac cttttgcctg catacagacg tcacgtgtcg   3060
tacggcagcc gaagtggccg tataccagga cgtgtatgct gtacatgcac caacatcgct   3120
gtaccatcag gcgatgaaag gtgtcagaac ggcgtattgg attgggtttg acaccacccc   3180
gtttatgttt gacgcgctag caggcgcgta tccaacctac gccacaaact gggccgacga   3240
gcaggtgtta caggccagga acataggact gtgtgcagca tccttgactg agggaagact   3300
cggcaaactg tccattctcc gcaagaagca attgaaacct tgcgacacag tcatgttctc   3360
ggtaggatct acattgtaca ctgagagcag aaagctactg aggagctggc acttaccctc   3420
cgtattccac ctgaaaggta aacaatcctt tacctgtagg tgcgatacca tcgtatcatg   3480
tgaagggtac gtagttaaga aaatcactat gtgccccggc ctgtacggta aaacggtagg   3540
gtacgccgtg acgtatcacg cggagggatt cctagtgtgc aagaccacag acactgtcaa   3600
aggagaaaga gtctcattcc ctgtatgcac ctacgtcccc tcaaccatct gtgatcaaat   3660
gactggcata ctagcgaccg acgtcacacc ggaggacgca cagaagttgt tagtgggatt   3720
gaatcagagg atagttgtga acggaagaac acagcgaaac actaacacga tgaagaacta   3780
tctgcttccg attgtggccg tcgcatttag caagtgggcg agggaataca aggcagacct   3840
tgatgatgaa aaacctctgg gtgtccgaga gaggtcactt acttgctgct gcttgtgggc   3900
atttaaaacg aggaagatgc acaccatgta caagaaacca gacacccaga caatagtgaa   3960
ggtgccttca gagtttaact cgttcgtcat cccgagccta tggtctacag gcctcgcaat   4020
cccagtcaga tcacgcatta agatgctttt ggccaagaag accaagcgag agttaatacc   4080
```

-continued

```
tgttctcgac gcgtcgtcag ccagggatgc tgaacaagag gagaaggaga ggttggaggc   4140
cgagctgact agagaagcct taccacccct cgtccccatc gcgccggcgg agacgggagt   4200
cgtcgacgtc gacgttgaag aactagagta tcacgcaggt gcaggggtcg tggaaacacc   4260
tcgcagcgcg ttgaaagtca ccgcacagcc gaacgacgta ctactaggaa attacgtagt   4320
tctgtccccg cagaccgtgc tcaagagctc caagttggcc cccgtgcacc ctctagcaga   4380
gcaggtgaaa ataataacac ataacgggag ggccggcggt taccaggtcg acggatatga   4440
cggcagggtc ctactaccat gtggatcggc cattccggtc cctgagtttc aagctttgag   4500
cgagagcgcc actatggtgt acaacgaaag ggagttcgtc aacaggaaac tataccatat   4560
tgccgttcac ggaccgtcgc tgaacaccga cgaggagaac tacgagaaag tcagagctga   4620
aagaactgac gccgagtacg tgttcgacgt agataaaaaa tgctgcgtca agagagagga   4680
agcgtcgggt ttggtgttgg tgggagagct aaccaacccc ccgttccatg aattcgccta   4740
cgaagggctg aagatcaggc cgtcggcacc atataagact acagtagtag gagtctttgg   4800
ggttccggga tcaggcaagt ctgctattat taagagcctc gtgaccaaac acgatctggt   4860
caccagcggc aagaaggaga actgccagga aatagttaac gacgtgaaga agcaccgcgg   4920
gaaggggaca agtagggaaa acagtgactc catcctgcta aacgggtgtc gtcgtgccgt   4980
ggacatccta tatgtggacg aggctttcgc ttgccattcc ggtactctgc tggccctaat   5040
tgctcttgtt aaacctcgga gcaaagtggt gttatgcgga gaccccaagc aatgcggatt   5100
cttcaatatg atgcagctta aggtgaactt caaccacaac atctgcactg aagtatgtca   5160
taaaagtata tccagacgtt gcacgcgtcc agtcacggcc atcgtgtcta cgttgcacta   5220
cggaggcaag atgcgcacga ccaacccgtg caacaaaccc ataatcatag acaccacagg   5280
acagaccaag cccaagccag gagacatcgt gttaacatgc ttccgaggct gggcaaagca   5340
gctgcagttg gactaccgtg gacacgaagt catgacagca gcagcatctc agggcctcac   5400
ccgcaaaggg gtatacgccg taaggcagaa ggtgaatgaa aatcccttgt atgcccctgc   5460
gtcggagcac gtgaatgtac tgctgacgcg cactgaggat aggctggtgt ggaaaacgct   5520
ggccggcgat ccctggatta aggtcctatc aaacattcca cagggtaact ttacggccac   5580
attggaagaa tggcaagaag aacacgacaa aataatgaag gtgattgaag gaccggctgc   5640
gcctgtggac gcgttccaga acaaagcgaa cgtgtgttgg gcgaaaagcc tggtgcctgt   5700
cctggacact gccggaatca gattgacagc agaggagtgg agcaccataa ttacagcatt   5760
taaggaggac agagcttact ctccagtggt ggccttgaat gaaatttgca ccaagtacta   5820
tggagttgac ctggacagtg gcctgttttc tgccccgaag gtgtccctgt attacgagaa   5880
caaccactgg gataacagac ctggtggaag gatgtatgga ttcaatgccg caacagctgc   5940
caggctggaa gctagacata ccttcctgaa ggggcagtgg catacgggca agcaggcagt   6000
tatcgcagaa agaaaaatcc aaccgctttc tgtgctggac aatgtaattc ctatcaaccg   6060
caggctgccg cacgccctgg tggctgagta caagacggtt aaaggcagta gggttgagtg   6120
gctggtcaat aaagtaagag ggtaccacgt cctgctggtg agtgagtaca acctggcttt   6180
gcctcgacgc agggtcactt ggttgtcacc gctgaatgtc acaggcgccg ataggtgcta   6240
cgacctaagt ttaggactgc cggctgacgc cggcaggttc gacttggtct ttgtgaacat   6300
tcacacggaa ttcagaatcc accactacca gcagtgtgtc gaccacgcca tgaagctgca   6360
gatgcttggg ggagatgcgc tacgactgct aaaacccggc ggcatcttga tgagagctta   6420
```

-continued

```
cggatacgcc gataaaatca gcgaagccgt tgtttcctcc ttaagcagaa agttctcgtc   6480
tgcaagagtg ttgcgcccgg attgtgtcac cagcaataca gaagtgttct tgctgttctc   6540
caactttgac aacggaaaga gaccctctac gctacaccag atgaatacca agctgagtgc   6600
cgtgtatgcc ggagaagcca tgcacacggc cgggtgtgca ccatcctaca gagttaagag   6660
agcagacata gccacgtgca cagaagcggc tgtggttaac gcagctaacg cccgtggaac   6720
tgtaggggat ggcgtatgca gggccgtggc gaagaaatgg ccgtcagcct ttaagggagc   6780
agcaacacca gtgggcacaa ttaaaacagt catgtgcggc tcgtaccccg tcatccacgc   6840
tgtagcgcct aatttctctg ccacgactga agcggaaggg gaccgcgaat tggccgctgt   6900
ctaccgggca gtggccgccg aagtaaacag actgtcactg agcagcgtag ccatcccgct   6960
gctgtccaca ggagtgttca gcggcggaag agataggctg cagcaatccc tcaaccatct   7020
attcacagca atggacgcca cggacgctga cgtgaccatc tactgcagag acaaaagttg   7080
ggagaagaaa atccaggaag ccattgacat gaggacggct gtggagttgc tcaatgatga   7140
cgtggagctg accacagact tggtgagagt gcacccggac agcagcctgg tgggtcgtaa   7200
gggctacagt accactgacg ggtcgctgta ctcgtacttt gaaggtacga aattcaacca   7260
ggctgctatt gatatggcag agatactgac gttgtggccc agactgcaag aggcaaacga   7320
acagatatgc ctatacgcgc tgggcgaaac aatggacaac atcagatcca aatgtccggt   7380
gaacgattcc gattcatcaa cacctcccag gacagtgccc tgcctgtgcc gctacgcaat   7440
gacagcagaa cggatcgccc gccttaggtc acaccaagtt aaaagcatgg tggtttgctc   7500
atcttttccc ctcccgaaat accatgtaga tggggtgcag aaggtaaagt gcgagaaggt   7560
tctcctgttc gacccgacgg taccttcagt ggttagtccg cggaagtatg ccgcatctac   7620
gacggaccac tcagatcggt cgttacgagg gtttgacttg gactggacca ccgactcgtc   7680
ttccactgcc agcgatacca tgtcgctacc cagtttgcag tcgtgtgaca tcgactcgat   7740
ctacgagcca atggctccca tagtagtgac ggctgacgta caccctgaac ccgcaggcat   7800
cgcggacctg gcggcagatg tgcaccctga acccgcagac catgtggacc tcgagaaccc   7860
gattcctcca ccgcgcccga agagagctgc ataccttgcc tcccgcgcgg cggagcgacc   7920
ggtgccggcg ccgagaaagc cgacgcctgc cccaaggact gcgtttagga acaagctgcc   7980
tttgacgttc ggcgactttg acgagcacga ggtcgatgcg ttggcctccg ggattacttt   8040
cggagacttc gacgacgtcc tgcgactagg ccgcgcgggt gcatatattt tctcctcgga   8100
cactggcagc ggacatttac aacaaaaatc cgttaggcag cacaatctcc agtgcgcaca   8160
actggatgcg gtccaggagg agaaaatgta cccgccaaaa ttggatactg agagggagaa   8220
gctgttgctg ctgaaaatgc agatgcaccc atcggaggct aataagagtc gataccagtc   8280
tcgcaaagtg gagaacatga aagccacggt ggtggacagg ctcacatcgg gggccagatt   8340
gtacacggga gcggacgtag gccgcatacc aacatacgcg gttcggtacc cccgccccgt   8400
gtactcccct accgtgatcg aaagattctc aagccccgat gtagcaatcg cagcgtgcaa   8460
cgaataccta tccagaaatt acccaacagt ggcgtcgtac cagataacag atgaatacga   8520
cgcatacttg gacatggttg acgggtcgga tagttgcttg gacagagcga cattctgccc   8580
ggcgaagctc cggtgctacc cgaaacatca tgcgtaccac cagccgactg tacgcagtgc   8640
cgtcccgtca ccctttcaga acacactaca gaacgtgcta gcggccgcca ccaagagaaa   8700
ctgcaacgtc acgcaaatgc gagaactacc caccatggac tcggcagtgt tcaacgtgga   8760
gtgcttcaag cgctatgcct gctccggaga atattgggaa gaatatgcta aacaacctat   8820
```

```
ccggataacc actgagaaca tcactaccta tgtgaccaaa ttgaaaggcc cgaaagctgc   8880
tgccttgttc gctaagaccc acaacttggt tccgctgcag gaggttccca tggacagatt   8940
cacggtcgac atgaaacgag atgtcaaagt cactccaggg acgaaacaca cagaggaaag   9000
acccaaagtc caggtaattc aagcagcgga gccattggcg accgcttacc tgtgcggcat   9060
ccacagggaa ttagtaagga gactaaatgc tgtgttacgc cctaacgtgc acacattgtt   9120
tgatatgtcg gccgaagact ttgacgcgat catcgcctct cacttccacc caggagaccc   9180
ggttctagag acggacattg catcattcga caaaagccag gacgactcct tggctcttac   9240
aggtttaatg atcctcgaag atctaggggt ggatcagtac ctgctggact tgatcgaggc   9300
agcctttggg gaaatatcca gctgtcacct accaactggc acgcgcttca agttcggagc   9360
tatgatgaaa tcgggcatgt ttctgacttt gtttattaac actgttttga acatcaccat   9420
agcaagcagg gtactggagc agagactcac tgactccgcc tgtgcggcct tcatcggcga   9480
cgacaacatc gttcacggag tgatctccga caagctgatg gcggagaggt gcgcgtcgtg   9540
ggtcaacatg gaggtgaaga tcattgacgc tgtcatgggc gaaaaacccc catatttttg   9600
tgggggattc atagtttttg acagcgtcac acagaccgcc tgccgtgttt cagacccact   9660
taagcgcctg ttcaagttgg gtaagccgct aacagctgaa gacaagcagg acgaagacag   9720
gcgacgagca ctgagtgacg aggttagcaa gtggttccgg acaggcttgg gggccgaact   9780
ggaggtggca ctaacatcta ggtatgaggt agagggctgc aaaagtatcc tcatagccat   9840
ggccaccttg gcgagggaca ttaaggcgtt taagaaattg agaggacctg ttatacacct   9900
ctacggcggt cctagattgg tgcgttaata cacagaattc tgattggatc atagcgcact   9960
attataggat ccgcgcgcgc gaattcggca cgagtaacaa tggagttgct aatcctcaaa  10020
gcaaatgcaa ttaccacaat cctcactgca gtcacatttt gttttgcttc tggtcaaaac  10080
atcactgaag aattttatca atcaacatgc agtgcagtta gcaaaggcta tcttagtgct  10140
ctgagaactg gttggtatac cagtgttata actatagaat taagtaatat caaggaaaat  10200
aagtgtaatg gaacagatgc taaggtaaaa ttgataaaac aagaattaga taaatataaa  10260
aatgctgtaa cagaattgca gttgctcatg caaagcacac cagcagcaaa caatcgagcc  10320
agaagagaac taccaaggtt tatgaattat acactcaaca atgccaaaaa aaccaatgta  10380
acattaagca agaaaaggaa aagaagattt cttggttttt tgttaggtgt tggatctgca  10440
atcgccagtg gcgttgctgt atctaaggtc ctgcacctag aaggggaagt gaacaagatc  10500
aaaagtgctc tactatccac aaacaaggct gtagtcagct tatcaaatgg agttagtgtc  10560
ttaaccagca aagtgttaga cctcaaaaac tatatagata aacaattgtt acctattgtg  10620
aacaagcaaa gctgcagcat atcaaatata gaaactgtga tagagttcca acaaaagaac  10680
aacagactac tagagattac cagggaattt agtgttaatg caggtgtaac tacacctgta  10740
agcacttaca tgttaactaa tagtgaatta ttgtcattaa tcaatgatat gcctataaca  10800
aatgatcaga aaaagttaat gtccaacaat gttcaaatag ttagacagca aagttactct  10860
atcatgtcca taataaaaga ggaagtctta gcatatgtag tacaattacc actatatggt  10920
gttatagata caccctgttg gaaactacac acatcccctc tatgtacaac caacacaaaa  10980
gaagggtcca acatctgttt aacaagaact gacagaggat ggtactgtga caatgcagga  11040
tcagtatctt tcttcccaca agctgaaaca tgtaaagttc aatcaaatcg agtattttgt  11100
gacacaatga acagtttaac attaccaagt gaaataaatc tctgcaatgt tgacatattc  11160
```

-continued

```
aaccccaaat atgattgtaa aattatgact tcaaaaacag atgtaagcag ctccgttatc  11220
acatctctag gagccattgt gtcatgctat ggcaaaacta aatgtacagc atccaataaa  11280
aatcgtggaa tcataaagac attttctaac gggtgcgatt atgtatcaaa taaagggatg  11340
gacactgtgt ctgtaggtaa cacattatat tatgtaaata agcaagaagg taaaagtctc  11400
tatgtaaaag gtgaaccaat aataaatttc tatgacccat tagtattccc ctctgatgaa  11460
tttgatgcat caatatctca agtcaacgag aagattaacc agagcctagc atttattcgt  11520
aaatccgatg aattattaca taatgtaaat gctggtaaat ccaccacaaa tatcatgact  11580
tgataatgag gatccagatc ccgggtaatt aattgaatta catccctacg caaacgtttt  11640
acggccgccg gtggcgcccg cgcccggcgg cccgtccttg gccgttgcag gccactccgg  11700
tggctcccgt cgtccccgac ttccaggccc agcagatgca gcaactcatc agcgccgtaa  11760
atgcgctgac aatgagacag aacgcaattg ctcctgctag gcctcccaaa ccaaagaaga  11820
agaagacaac caaaccaaag ccgaaaacgc agcccaagaa gatcaacgga aaaacgcagc  11880
agcaaaagaa gaaagacaag caagccgaca agaagaagaa gaaacccgga aaaagagaaa  11940
gaatgtgcat gaagattgaa aatgactgta tcttcgtatg cggctagcca cagtaacgta  12000
gtgtttccag acatgtcggg caccgcacta tcatgggtgc agaaaatctc gggtggtctg  12060
ggggccttcg caatcggcgc tatcctggtg ctggttgtgg tcacttgcat tgggctccgc  12120
agataagtta gggtaggcaa tggcattgat atagcaagaa aattgaaaac agaaaaagtt  12180
agggtaagca atggcatata accataactg tataacttgt aacaaagcgc aacaagacct  12240
gcgcaattgg ccccgtggtc cgcctcacgg aaactcgggg caactcatat tgacacatta  12300
attggcaata attggaagct tacataagct taattcgacg aataattgga tttttatttt  12360
attttgcaat tggtttttaa tatttccaaa aaaaaaaaaa aaaaaaaaaa aaaaaaaaaa  12420
aaaaaaaaaa aaaaaaaaaa aaaaaaaaaa aaaaaaacta gcgggtcggc atggcatctc  12480
cacctcctcg cggtccgacc tgggcatccg aaggaggacg cacgtccact cggatggcta  12540
agggagagat ccagatctgc tgtgccttct agttgccagc catctgttgt ttgcccctcc  12600
cccgtgcctt ccttgaccct ggaaggtgcc actcccactg tcctttccta ataaaatgag  12660
gaaattgcat cgcattgtct gagtaggtgt cattctattc tggggggtgg ggtggggcag  12720
gacagcaagg gggaggattg ggaagacaat agcaggcatg ctggggatgc ggtgggctct  12780
atgggtaccc aggtgctgaa gaattgaccc ggttcctcct gggccagaaa gaagcaggca  12840
catccccttc tctgtgacac accctgtcca cgcccctggt tcttagttcc agccccactc  12900
ataggacact catagctcag gagggctccg ccttcaatcc cacccgctaa agtacttgga  12960
gcggtctctc cctccctcat cagcccacca aaccaaacct agcctccaag agtgggaaga  13020
aattaaagca agataggcta ttaagtgcag agggagagaa aatgcctcca acatgtgagg  13080
aagtaatgag agaaatcata gaatttcttc cgcttcctcg ctcactgact cgctgcgctc  13140
ggtcgttcgg ctgcggcgag cggtatcagc tcactcaaag gcggtaatac ggttatccac  13200
agaatcaggg gataacgcag gaaagaacat gtgagcaaaa ggccagcaaa aggccaggaa  13260
ccgtaaaaag gccgcgttgc tggcgttttt ccataggctc cgcccccctg acgagcatca  13320
caaaaatcga cgctcaagtc agaggtggcg aaacccgaca ggactataaa gataccaggc  13380
gtttccccct ggaagctccc tcgtgcgctc tcctgttccg accctgccgc ttaccggata  13440
cctgtccgcc tttctccctt cgggaagcgt ggcgctttct catagctcac gctgtaggta  13500
tctcagttcg gtgtaggtcg ttcgctccaa gctgggctgt gtgcacgaac cccccgttca  13560
```

-continued

```
gcccgaccgc tgcgccttat ccggtaacta tcgtcttgag tccaacccgg taagacacga  13620
cttatcgcca ctggcagcag ccactggtaa caggattagc agagcgaggt atgtaggcgg  13680
tgctacagag ttcttgaagt ggtggcctaa ctacggctac actagaagaa cagtatttgg  13740
tatctgcgct ctgctgaagc cagttacctt cggaaaaaga gttggtagct cttgatccgg  13800
caaacaaacc accgctggta gcggtggttt ttttgtttgc aagcagcaga ttacgcgcag  13860
aaaaaaagga tctcaagaag atcctttgat cttttctacg gggtctgacg ctcagtggaa  13920
cgaaaactca cgttaaggga ttttggtcat gagattatca aaaaggatct tcacctagat  13980
ccttttaaat taaaaatgaa gttttaaatc aatctaaagt atatatgagt aaacttggtc  14040
tgacagttac caatgcttaa tcagtgaggc acctatctca gcgatctgtc tatttcgttc  14100
atccatagtt gcctgactcg gggggggggg gcgctgaggt ctgcctcgtg aagaaggtgt  14160
tgctgactca taccaggcct gaatcgcccc atcatccagc cagaaagtga gggagccacg  14220
gttgatgaga gctttgttgt aggtggacca gttggtgatt ttgaactttt gctttgccac  14280
ggaacggtct gcgttgtcgg gaagatgcgt gatctgatcc ttcaactcag caaaagttcg  14340
atttattcaa caaagccgcc gtcccgtcaa gtcagcgtaa tgctctgcca gtgttacaac  14400
caattaacca attgtgatta gaaaaactca tcgagcatca aatgaaactg caatttattc  14460
atatcaggat tatcaatacc atatttttga aaaagccgtt tctgtaatga aggagaaaac  14520
tcaccgaggc agttccatag gatggcaaga tcctggtatc ggtctgcgat tccgactcgt  14580
ccaacatcaa tacaacctat taatttcccc tcgtcaaaaa taaggttatc aagtgagaaa  14640
tcaccatgag tgacgactga atccggtgag aatggcaaaa gcttatgcat ttctttccag  14700
acttgttcaa caggccagcc attacgctcg tcatcaaaat cactcgcatc aaccaaaccg  14760
ttattcattc gtgattgcgc ctgagcgaga cgaaatacgc gatcgctgtt aaaaggacaa  14820
ttacaaacag gaatcgaatg caaccggcgc aggaacactg ccagcgcatc aacaatattt  14880
tcacctgaat caggatattc ttctaatacc tggaatgctg ttttcccggg gatcgcagtg  14940
gtgagtaacc atgcatcatc aggagtacgg ataaaatgct tgatggtcgg aagaggcata  15000
aattccgtca gccagtttag tctgaccatc tcatctgtaa catcattggc aacgctacct  15060
ttgccatgtt tcagaaacaa ctctggcgca tcgggcttcc catacaatcg atagattgtc  15120
gcacctgatt gcccgacatt atcgcgagcc catttatacc catataaatc agcatccatg  15180
ttggaattta atcgcggcct cgagcaagac gtttcccgtt gaatatggct cataacgttc  15240
cttgtattac tgtttatgta agcagacagt tttattgttc atgatgatat atttttatct  15300
tgtgcaatgt aacatcagag attttgagac acaacgtggc tttccccccc cccccattat  15360
tgaagcattt atcagggtta ttgtctcatg agcggataca tatttgaatg tatttagaaa  15420
aataaacaaa taggggttcc gcgcacattt ccccgaaaag tgccacctga cgtctaagaa  15480
accattatta tcatgacatt aacctataaa aataggcgta tcacgaggcc ctttcgtc    15538
```

<210> SEQ ID NO 2
<211> LENGTH: 90
<212> TYPE: DNA
<213> ORGANISM: respiratory syncytial virus

<400> SEQUENCE: 2

```
ctagcgggtc ggcatggcat ctccacctcc tcgcggtccg acctgggcat ccgaaggagg     60
acgcacgtcc actcggatgg ctaagggaga                                       90
```

<210> SEQ ID NO 3
<211> LENGTH: 90
<212> TYPE: DNA
<213> ORGANISM: respiratory syncytial virus

<400> SEQUENCE: 3

```
gcccagccgt accgtagagg ttgaggagcg ccaggctgga cccgtaggct tcctcctgcg     60

tgcaggtgag cctaccgatt ccctctctag                                      90
```

<210> SEQ ID NO 4
<211> LENGTH: 8100
<212> TYPE: DNA
<213> ORGANISM: respiratory syncytial virus

<400> SEQUENCE: 4

```
atcggcagtg cgccttccag gagaatgatg tctacgcaca aataccactg cgtatgccct     60

atgcgcagcg cagaagaccc cgaaaggctc gatagctacg caaagaaact ggcagcggcc    120

tccgggaagg tgctggatag agagatcgca ggaaaaatca ccgacctgca gaccgtcatg    180

gctacgccag acgctgaatc tcctaccttt tgcctgcata cagacgtcac gtgtcgtacg    240

gcagccgaag tggccgtata ccaggacgtg tatgctgtac atgcaccaac atcgctgtac    300

catcaggcga tgaaaggtgt cagaacggcg tattggattg ggtttgacac caccccgttt    360

atgtttgacg cgctagcagg cgcgtatcca acctacgcca caaactgggc cgacgagcag    420

gtgttacagg ccaggaacat aggactgtgt gcagcatcct tgactgaggg aagactcggc    480

aaactgtcca ttctccgcaa gaagcaattg aaaccttgcg acacagtcat gttctcggta    540

ggatctacat tgtacactga gagcagaaag ctactgagga gctggcactt accctccgta    600

ttccacctga aaggtaaaca atcctttacc tgtaggtgcg ataccatcgt atcatgtgaa    660

gggtacgtag ttaagaaaat cactatgtgc cccggcctgt acggtaaaac ggtagggtac    720

gccgtgacgt atcacgcgga gggattccta gtgtgcaaga ccacagacac tgtcaaagga    780

gaaagagtct cattccctgt atgcacctac gtccccctcaa ccatctgtga tcaaatgact    840

ggcatactag cgaccgacgt cacaccggag gacgcacaga agttgttagt gggattgaat    900

cagaggatag ttgtgaacgg aagaacacag cgaaacacta acacgatgaa gaactatctg    960

cttccgattg tggccgtcgc atttagcaag tgggcgaggg aatacaaggc agaccttgat   1020

gatgaaaaac ctctgggtgt ccgagagagg tcacttactt gctgctgctt gtgggcattt   1080

aaaacgagga agatgcacac catgtacaag aaaccagaca cccagacaat agtgaaggtg   1140

ccttcagagt ttaactcgtt cgtcatcccg agcctatggt ctacaggcct cgcaatccca   1200

gtcagatcac gcattaagat gcttttggcc aagaagacca agcgagagtt aatacctgtt   1260

ctcgacgcgt cgtcagccag ggatgctgaa caagaggaga aggagaggtt ggaggccgag   1320

ctgactagag aagccttacc acccctcgtc cccatcgcgc cggcggagac gggagtcgtc   1380

gacgtcgacg ttgaagaact agagtatcac gcaggtgcag ggtcgtggga aacacctcgc   1440

agcgcgttga aagtcaccgc acagccgaac gacgtactac taggaaatta cgtagttctg   1500

tccccgcaga ccgtgctcaa gagctccaag ttggcccccg tgcaccctct agcagagcag   1560

gtgaaaataa taacacataa cgggagggcc ggcggttacc aggtcgacgg atatgacggc   1620

agggtcctac taccatgtgg atcggccatt ccggtccctg agtttcaagc tttgagcgag   1680

agcgccacta tggtgtacaa cgaaagggag ttcgtcaaca ggaaactata ccatattgcc   1740
```

-continued

```
gttcacggac cgtcgctgaa caccgacgag gagaactacg agaaagtcag agctgaaaga   1800
actgacgccg agtacgtgtt cgacgtagat aaaaaatgct gcgtcaagag agaggaagcg   1860
tcgggtttgg tgttggtggg agagctaacc aaccccccgt tccatgaatt cgcctacgaa   1920
gggctgaaga tcaggccgtc ggcaccatat aagactacag tagtaggagt ctttggggtt   1980
ccgggatcag gcaagtctgc tattattaag agcctcgtga ccaaacacga tctggtcacc   2040
agcggcaaga aggagaactg ccaggaaata gttaacgacg tgaagaagca ccgcgggaag   2100
gggacaagta gggaaaacag tgactccatc ctgctaaacg ggtgtcgtcg tgccgtggac   2160
atcctatatg tggacgaggc tttcgcttgc cattccggta ctctgctggc cctaattgct   2220
cttgttaaac ctcggagcaa agtggtgtta tgcggagacc ccaagcaatg cggattcttc   2280
aatatgatgc agcttaaggt gaacttcaac cacaacatct gcactgaagt atgtcataaa   2340
agtatatcca gacgttgcac gcgtccagtc acggccatcg tgtctacgtt gcactacgga   2400
ggcaagatgc gcacgaccaa cccgtgcaac aaacccataa tcatagacac cacaggacag   2460
accaagccca agccaggaga catcgtgtta acatgcttcc gaggctgggc aaagcagctg   2520
cagttggact accgtggaca cgaagtcatg acagcagcag catctcaggg cctcacccgc   2580
aaaggggtat acgccgtaag gcagaaggtg aatgaaaatc ccttgtatgc ccctgcgtcg   2640
gagcacgtga atgtactgct gacgcgcact gaggataggc tggtgtggaa aacgctggcc   2700
ggcgatccct ggattaaggt cctatcaaac attccacagg gtaactttac ggccacattg   2760
gaagaatggc aagaagaaca cgacaaaata atgaaggtga ttgaaggacc ggctgcgcct   2820
gtggacgcgt tccagaacaa agcgaacgtg tgttgggcga aaagcctggt gcctgtcctg   2880
gacactgccg gaatcagatt gacagcagag gagtggagca ccataattac agcatttaag   2940
gaggacagag cttactctcc agtggtggcc ttgaatgaaa tttgcaccaa gtactatgga   3000
gttgacctgg acagtggcct gttttctgcc ccgaaggtgt ccctgtatta cgagaacaac   3060
cactgggata acagacctgg tggaaggatg tatggattca atgccgcaac agctgccagg   3120
ctggaagcta gacatacctt cctgaagggg cagtggcata cgggcaagca ggcagttatc   3180
gcagaaagaa aaatccaacc gctttctgtg ctggacaatg taattcctat caaccgcagg   3240
ctgccgcacg ccctggtggc tgagtacaag acggttaaag gcagtagggt tgagtggctg   3300
gtcaataaag taagagggta ccacgtcctg ctggtgagtg agtacaacct ggctttgcct   3360
cgacgcaggg tcacttggtt gtcaccgctg aatgtcacag gcgccgatag gtgctacgac   3420
ctaagtttag gactgccggc tgacgccggc aggttcgact tggtctttgt gaacattcac   3480
acggaattca gaatccacca ctaccagcag tgtgtcgacc acgccatgaa gctgcagatg   3540
cttgggggag atgcgctacg actgctaaaa cccggcggca tcttgatgag agcttacgga   3600
tacgccgata aaatcagcga agccgttgtt tcctccttaa gcagaaagtt ctcgtctgca   3660
agagtgttgc gcccggattg tgtcaccagc aatacagaag tgttcttgct gttctccaac   3720
tttgacaacg gaaagagacc ctctacgcta caccagatga ataccaagct gagtgccgtg   3780
tatgccggag aagccatgca cacggccggg tgtgcaccat cctacagagt taagagagca   3840
gacatagcca cgtgcacaga agcggctgtg gttaacgcag ctaacgcccg tggaactgta   3900
ggggatggcg tatgcagggc cgtggcgaag aaatggccgt cagcctttaa gggagcagca   3960
acaccagtgg gcacaattaa aacagtcatg tgcggctcgt accccgtcat ccacgctgta   4020
gcgcctaatt tctctgccac gactgaagcg gaaggggacc gcgaattggc cgctgtctac   4080
cgggcagtgg ccgccgaagt aaacagactg tcactgagca gcgtagccat cccgctgctg   4140
```

-continued

```
tccacaggag tgttcagcgg cggaagagat aggctgcagc aatccctcaa ccatctattc   4200
acagcaatgg acgccacgga cgctgacgtg accatctact gcagagacaa aagttgggag   4260
aagaaaatcc aggaagccat tgacatgagg acggctgtgg agttgctcaa tgatgacgtg   4320
gagctgacca cagacttggt gagagtgcac ccggacagca gcctggtggg tcgtaagggc   4380
tacagtacca ctgacgggtc gctgtactcg tactttgaag gtacgaaatt caaccaggct   4440
gctattgata tggcagagat actgacgttg tggcccagac tgcaagaggc aaacgaacag   4500
atatgcctat acgcgctggg cgaaacaatg gacaacatca gatccaaatg tccggtgaac   4560
gattccgatt catcaacacc tcccaggaca gtgccctgcc tgtgccgcta cgcaatgaca   4620
gcagaacgga tcgcccgcct taggtcacac caagttaaaa gcatggtggt ttgctcatct   4680
tttcccctcc cgaaatacca tgtagatggg gtgcagaagg taaagtgcga gaaggttctc   4740
ctgttcgacc cgacggtacc ttcagtggtt agtccgcgga agtatgccgc atctacgacg   4800
gaccactcag atcggtcgtt acgagggttt gacttggact ggaccaccga ctcgtcttcc   4860
actgccagcg ataccatgtc gctacccagt ttgcagtcgt gtgacatcga ctcgatctac   4920
gagccaatgg ctcccatagt agtgacggct gacgtacacc ctgaacccgc aggcatcgcg   4980
gacctggcgg cagatgtgca ccctgaaccc gcagaccatg tggacctcga gaacccgatt   5040
cctccaccgc gcccgaagag agctgcatac cttgcctccc gcgcggcgga gcgaccggtg   5100
ccggcgccga gaaagccgac gcctgcccca aggactgcgt ttaggaacaa gctgcctttg   5160
acgttcggcg actttgacga gcacgaggtc gatgcgttgg cctccgggat tactttcgga   5220
gacttcgacg acgtcctgcg actaggccgc gcgggtgcat atattttctc ctcggacact   5280
ggcagcggac atttacaaca aaaatccgtt aggcagcaca atctccagtg cgcacaactg   5340
gatgcggtcc aggaggagaa aatgtacccg ccaaaattgg atactgagag ggagaagctg   5400
ttgctgctga aaatgcagat gcacccatcg gaggctaata agagtcgata ccagtctcgc   5460
aaagtggaga acatgaaagc cacggtggtg gacaggctca catcgggggc cagattgtac   5520
acgggagcgg acgtaggccg cataccaaca tacgcggttc ggtacccccg ccccgtgtac   5580
tcccctaccg tgatcgaaag attctcaagc cccgatgtag caatcgcagc gtgcaacgaa   5640
tacctatcca gaaattaccc aacagtggcg tcgtaccaga taacagatga atacgacgca   5700
tacttggaca tggttgacgg gtcggatagt tgcttggaca gagcgacatt ctgcccggcg   5760
aagctccggt gctacccgaa acatcatgcg taccaccagc cgactgtacg cagtgccgtc   5820
ccgtcaccct ttcagaacac actacagaac gtgctagcgg ccgccaccaa gagaaactgc   5880
aacgtcacgc aaatgcgaga actacccacc atggactcgg cagtgttcaa cgtggagtgc   5940
ttcaagcgct atgcctgctc cggagaatat tgggaagaat atgctaaaca acctatccgg   6000
ataaccactg agaacatcac tacctatgtg accaaattga aaggcccgaa agctgctgcc   6060
ttgttcgcta agacccacaa cttggttccg ctgcaggagg ttcccatgga cagattcacg   6120
gtcgacatga aacgagatgt caaagtcact ccagggacga aacacacaga ggaaagaccc   6180
aaagtccagg taattcaagc agcggagcca ttggcgaccg cttacctgtg cggcatccac   6240
agggaattag taaggagact aaatgctgtg ttacgcccta acgtgcacac attgtttgat   6300
atgtcggccg aagactttga cgcgatcatc gcctctcact tccacccagg agacccggtt   6360
ctagagacgg acattgcatc attcgacaaa agccaggacg actccttggc tcttacaggt   6420
ttaatgatcc tcgaagatct aggggtggat cagtacctgc tggacttgat cgaggcagcc   6480
```

-continued

```
tttggggaaa tatccagctg tcacctacca actggcacgc gcttcaagtt cggagctatg   6540

atgaaatcgg gcatgtttct gactttgttt attaacactg ttttgaacat caccatagca   6600

agcagggtac tggagcagag actcactgac tccgcctgtg cggccttcat cggcgacgac   6660

aacatcgttc acggagtgat ctccgacaag ctgatggcgg agaggtgcgc gtcgtgggtc   6720

aacatggagg tgaagatcat tgacgctgtc atgggcgaaa aacccccata tttttgtggg   6780

ggattcatag tttttgacag cgtcacacag accgcctgcc gtgtttcaga cccacttaag   6840

cgcctgttca agttgggtaa gccgctaaca gctgaagaca agcaggacga agacaggcga   6900

cgagcactga gtgacgaggt tagcaagtgg ttccggacag gcttgggggc cgaactggag   6960

gtggcactaa catctaggta tgaggtagag ggctgcaaaa gtatcctcat agccatggcc   7020

accttggcga gggacattaa ggcgtttaag aaattgagag gacctgttat acacctctac   7080

ggcggtccta gattggtgcg ttaatacaca gaattctgat tggatcatag cgcactatta   7140

taggatccag atcccgggta attaattgaa ttacatccct acgcaaacgt tttacggccg   7200

ccggtggcgc ccgcgcccgg cggcccgtcc ttggccgttg caggccactc cggtggctcc   7260

cgtcgtcccc gacttccagg cccagcagat gcagcaactc atcagcgccg taaatgcgct   7320

gacaatgaga cagaacgcaa ttgctcctgc taggcctccc aaaccaaaga agaagaagac   7380

aaccaaacca aagccgaaaa cgcagcccaa gaagatcaac ggaaaaacgc agcagcaaaa   7440

gaagaaagac aagcaagccg acaagaagaa gaagaaaccc ggaaaaagag aaagaatgtg   7500

catgaagatt gaaaatgact gtatcttcgt atgcggctag ccacagtaac gtagtgtttc   7560

cagacatgtc gggcaccgca ctatcatggg tgcagaaaat ctcgggtggt ctgggggcct   7620

tcgcaatcgg cgctatcctg gtgctggttg tggtcacttg cattgggctc cgcagataag   7680

ttagggtagg caatggcatt gatatagcaa gaaaattgaa aacagaaaaa gttagggtaa   7740

gcaatggcat ataaccataa ctgtataact tgtaacaaag cgcaacaaga cctgcgcaat   7800

tggccccgtg gtccgcctca cggaaactcg gggcaactca tattgacaca ttaattggca   7860

ataattggaa gcttacataa gcttaattcg acgaataatt ggatttttat tttattttgc   7920

aattggtttt taatatttcc aaaaaaaaaa aaaaaaaaaa aaaaaaaaaa aaaaaaaaaa   7980

aaaaaaaaaa aaaaaaaaaa aaaaaaaaaa ctagcgggtc ggcatggcat ctccacctcc   8040

tcgcggtccg acctgggcat ccgaaggagg acgcacgtcc actcggatgg ctaagggaga   8100
```

<210> SEQ ID NO 5
<211> LENGTH: 30
<212> TYPE: DNA
<213> ORGANISM: respiratory syncytial virus

<400> SEQUENCE: 5

```
tccacctcca agatatccaa gatgagtgtg                                     30
```

<210> SEQ ID NO 6
<211> LENGTH: 30
<212> TYPE: DNA
<213> ORGANISM: respiratory syncytial virus

<400> SEQUENCE: 6

```
tccacctcca agatatccaa gatgagtgtg                                     30
```

<210> SEQ ID NO 7
<211> LENGTH: 282
<212> TYPE: DNA
<213> ORGANISM: respiratory syncytial virus -continued

<400> SEQUENCE: 7

```
tcgacatggc ggatgtgtga catacacgac gccaaaagat tttgttccag ctcctgccac     60

ctccgctacg cgagagatta accacccacg atggccgcca aagtgcatgt tgatattgag    120

gctgacagcc cattcatcaa gtctttgcag aaggcatttc cgtcgttcga ggtggagtca    180

ttgcaggtca caccaaatga ccatgcaaat gccagagcat tttcgcacct ggctaccaaa    240

ttgatcgagc aggagactga caaagacaca ctcatcttgg at                       282
```